(12) United States Patent
Ramesh et al.

(10) Patent No.: US 7,211,602 B2
(45) Date of Patent: May 1, 2007

(54) TREATMENT OF NEURODEGENERATIVE DISORDERS THROUGH THE MODULATION OF THE POLYAMINE PATHWAY

(75) Inventors: Tennore Ramesh, Westwood, MA (US); Sean Scott, San Francisco, CA (US)

(73) Assignee: ALS Therapy Development Foundation, Inc., Cambridge, MA (US)

( * ) Notice: Subject to any disclaimer, the term of this patent is extended or adjusted under 35 U.S.C. 154(b) by 472 days.

(21) Appl. No.: 10/286,631

(22) Filed: Nov. 1, 2002

(65) Prior Publication Data

US 2003/0158262 A1 Aug. 21, 2003

Related U.S. Application Data

(60) Provisional application No. 60/333,263, filed on Nov. 16, 2001.

(51) Int. Cl.
*A61K 31/17* (2006.01)

(52) U.S. Cl. .................................................. 514/588

(58) Field of Classification Search ............... 514/482, 514/575, 673, 588
See application file for complete search history.

(56) References Cited

U.S. PATENT DOCUMENTS

| | | | |
|---|---|---|---|
| 4,499,072 A | 2/1985 | Sunkara et al. | |
| 5,541,230 A | 7/1996 | Basu et al. | |
| 5,637,768 A | 6/1997 | Jund et al. | |
| 5,646,188 A | 7/1997 | Gilad et al. | |
| 5,677,349 A | 10/1997 | Gilad et al. | |
| 5,770,625 A | 6/1998 | Nakanishi et al. | |
| 5,880,161 A | 3/1999 | Basu et al. | |
| 5,886,051 A | 3/1999 | Bergeron, Jr. et al. | |
| 5,962,533 A | 10/1999 | Bergeron, Jr. | |
| 6,166,079 A | 12/2000 | Follen et al. | |

(Continued)

FOREIGN PATENT DOCUMENTS

EP 0 434 173 A2 12/1989

(Continued)

OTHER PUBLICATIONS

Bercovich, Zippy et al. "Regulation of Intracellular Polyamines, Polycations That Are Essential For Cellular Viability And Proliferation", Cell and Developmental Biology, pp. 110-111.

(Continued)

*Primary Examiner*—Shengjun Wang
(74) *Attorney, Agent, or Firm*—Thomas J. Engellenner; Deborah A. Miller; Nutter McClennen & Fish, LLP

(57) ABSTRACT

The present invention provides methods and compositions for modulating polyamine pathway activity as a means for ameliorating neurodegenarative disorders. In particular, for ameliorating the symptoms or onset of amyotrophic lateral sclerosis (ALS) by modulating the gene and protein products involved the polyamine pathway, such as by inhibiting the enzyme, ornithine decarboxylase (ODC), involved in the synthesis of the polyamine, putrescine. Compositions and methods are disclosed for inhibiting the polyamine pathway producing lower polyamine levels resulting in a beneficial effect on ALS. This can be accomplished by using modulating agents such as analogs, or polyamine analogs, and antiproliferative drugs. Screening assays for pharmacological agents that are capable of decreasing polyamine levels and/or reducing cell proliferation are also disclosed.

4 Claims, 13 Drawing Sheets

U.S. PATENT DOCUMENTS

| | | |
|---|---|---|
| 6,172,261 B1 | 1/2001 | Vermeulin et al. |
| 6,184,232 B1 | 2/2001 | Bergeron, Jr. |
| 6,194,000 B1 | 2/2001 | Smith et al. |
| 6,235,794 B1 | 5/2001 | Bergeron, Jr. |
| 6,277,411 B1 | 8/2001 | Shaked et al. |
| 6,342,534 B1 | 1/2002 | Bergeron, Jr. |
| 6,392,098 B1 | 5/2002 | Frydman et al. |
| 6,423,754 B1 | 7/2002 | Holmes-Farley et al. |

FOREIGN PATENT DOCUMENTS

| | | |
|---|---|---|
| EP | 0 361 687 A1 | 4/1990 |
| EP | 0 436 332 A3 | 7/1991 |
| EP | 0436 332 A2 | 7/1991 |
| EP | 0 950 406 A2 | 10/1999 |
| EP | 0 950 406 A3 | 11/1999 |
| JP | 07024965 | 8/1996 |
| WO | WO 99/08519 | 2/1999 |
| WO | WO 99/21542 | 5/1999 |
| WO | WO 99/65516 | 12/1999 |
| WO | WO 00/66587 | 11/2000 |
| WO | WO 01/85981 A2 | 11/2001 |
| WO | WO 01/85981 A3 | 11/2001 |
| WO | WO 02/053519 A3 | 7/2002 |

OTHER PUBLICATIONS

Gonzalez Deniselle, Maria Claudia et al. "Glucocorticoid Receptors And Actions In The Spinal Cord of the Wobbler Mouse, a Model for Neurodegenerative Diseases", J. Steroid Biochem. Molec. Biol., vol. 60, No. 3-4, pp. 205-213 (1997).

Scorcioni, Francesca et al. "Manipulation of the Expression of Regulatory Genes of Polyamine Metabolism Results in Specific Alterations of the Cell-Cycle Progression", Biochem. J. vol. 354, pp. 217-223 (2001).

Thomas T. and Thomas T.J., "Polyamines in Cell Growth and Cell Death: Molecular Mechanisms and Therapeutic Applications", CMLS, Cell. Mol. Life Sci., vol. 58, pp. 244-258 (2001).

Figure 4A and B.
4A.
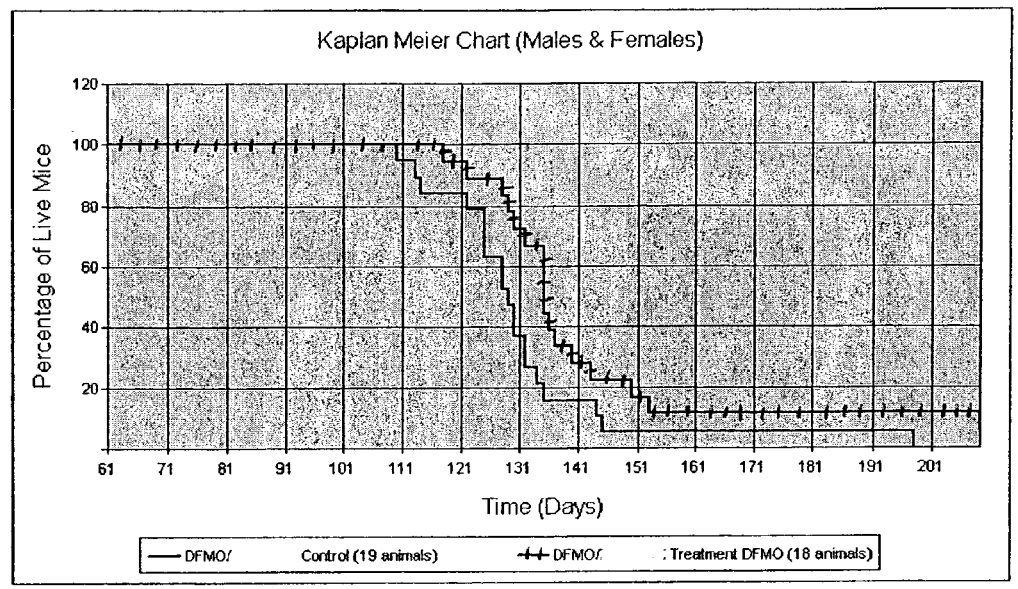
4B.
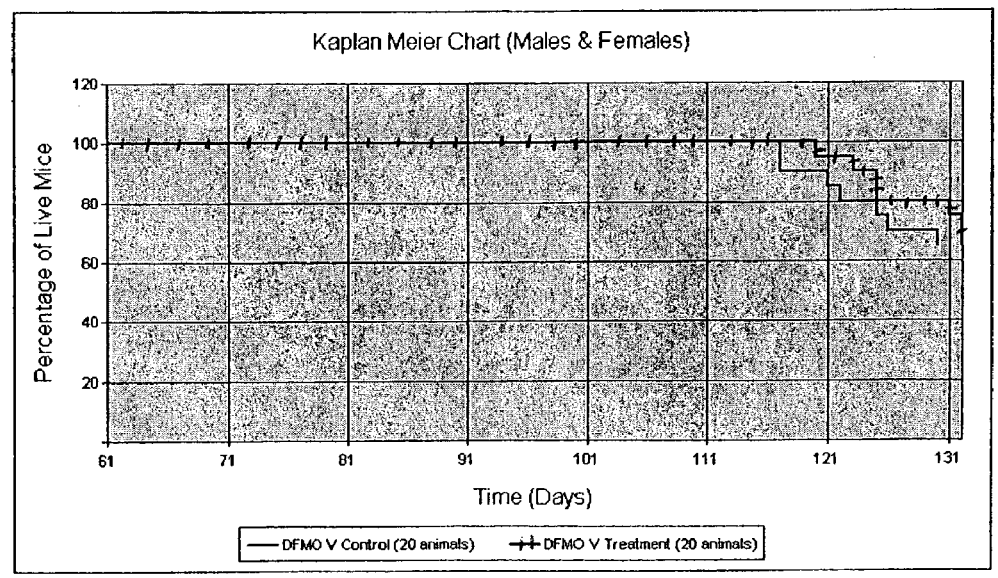

Figure 5A and B.
5A.
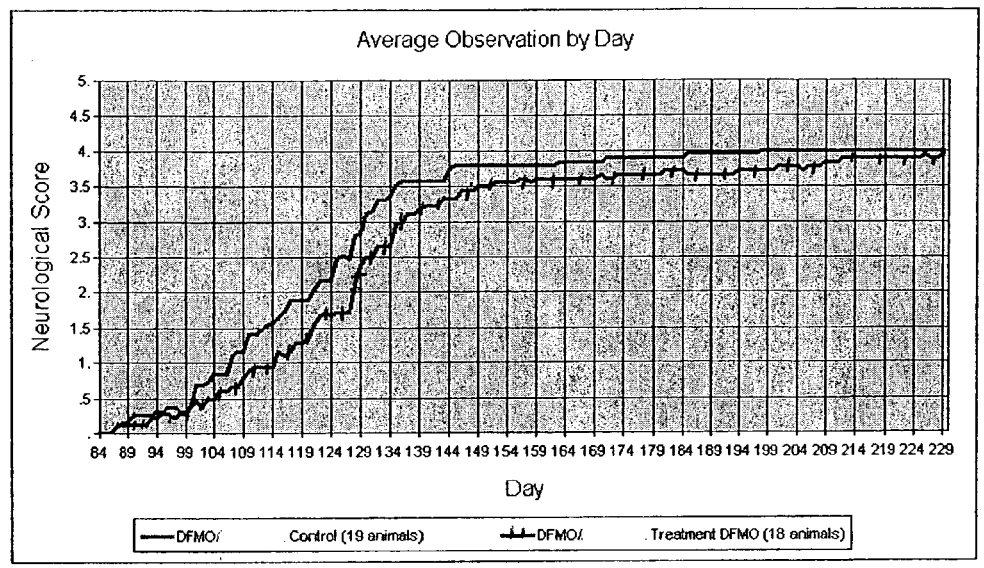
5B.
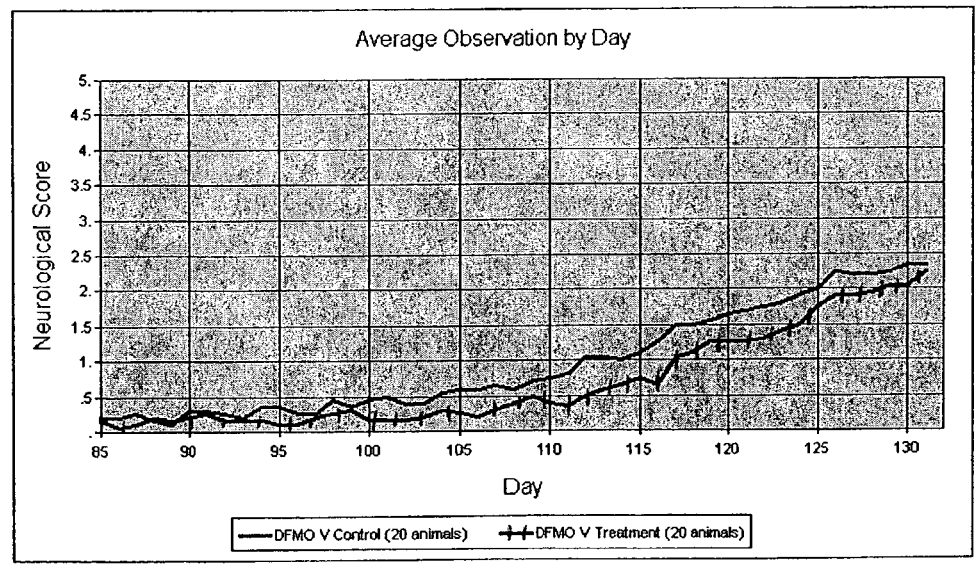

Figure 6A and B.
6A.
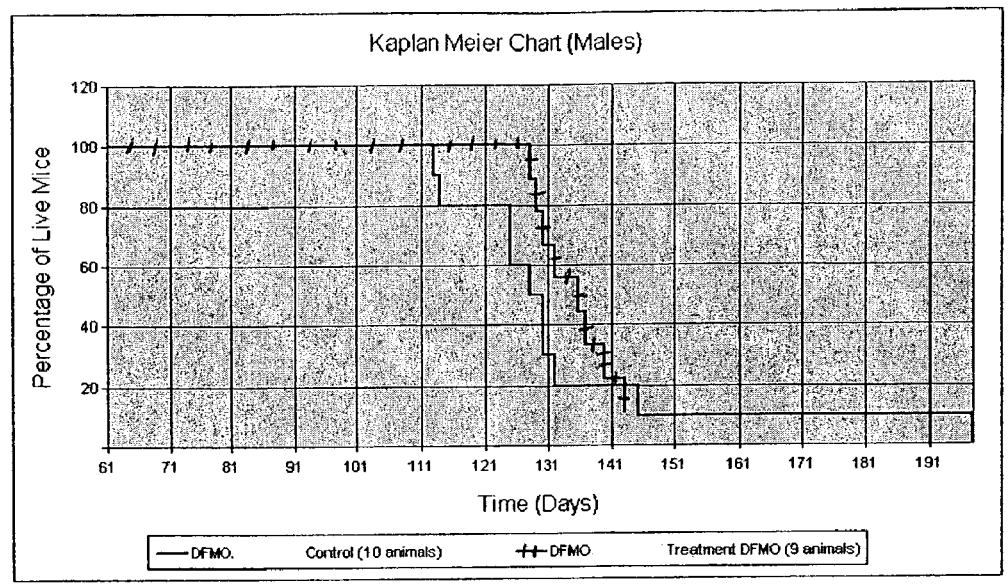
6B.
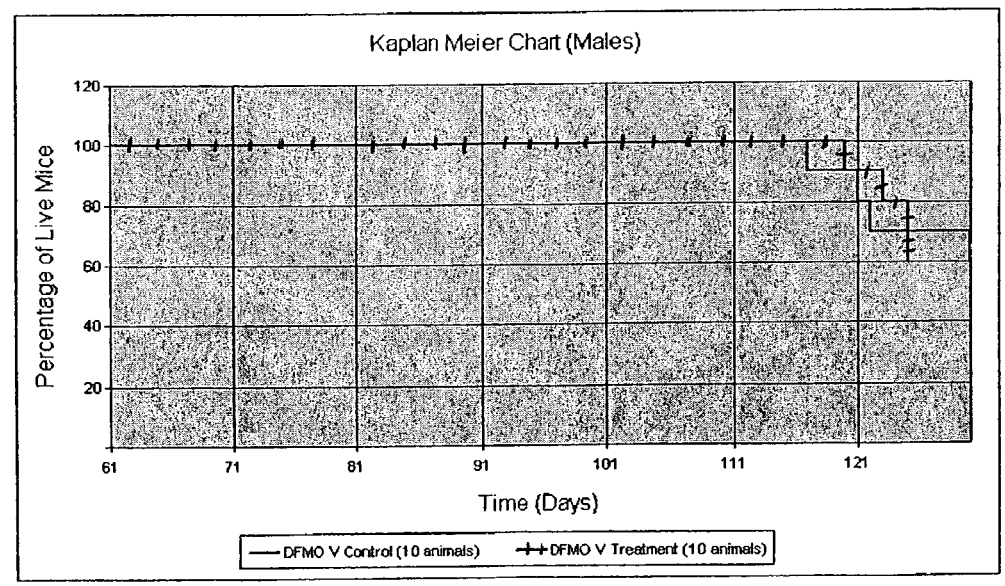

Figure 7A and B.
7A.
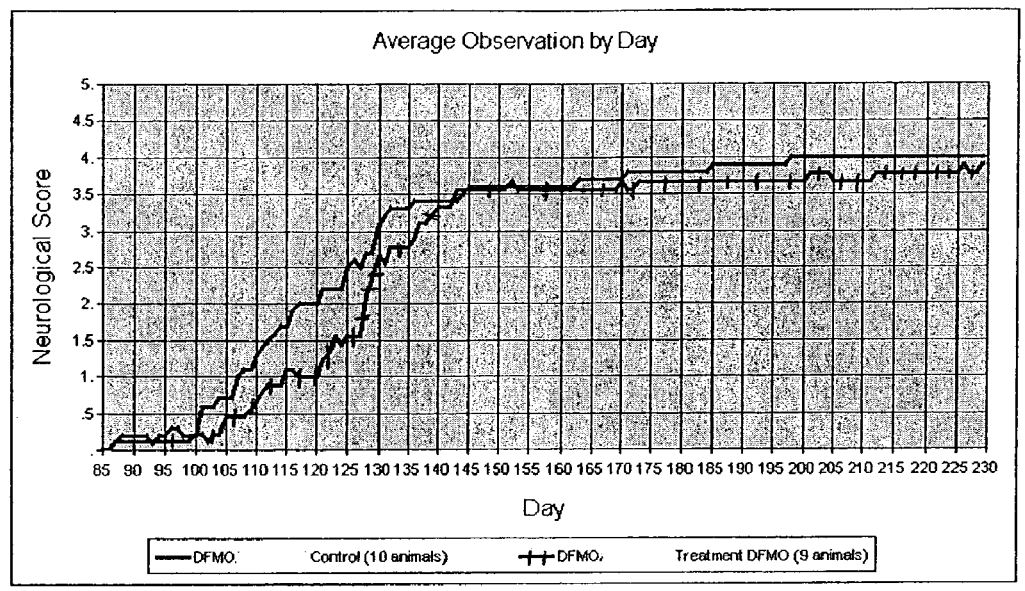
7B.
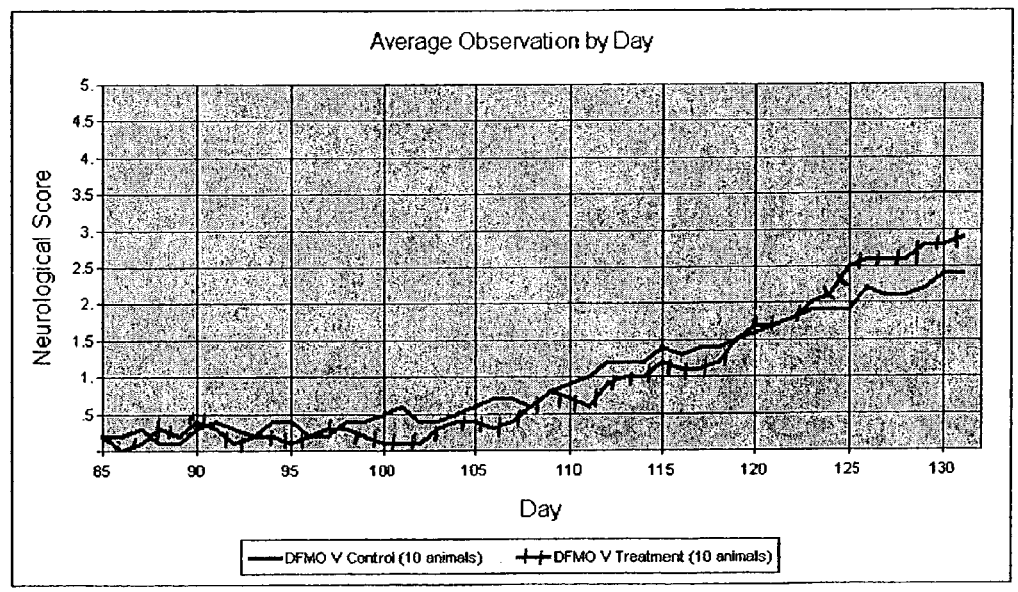

Figure 8A and B.
8A.
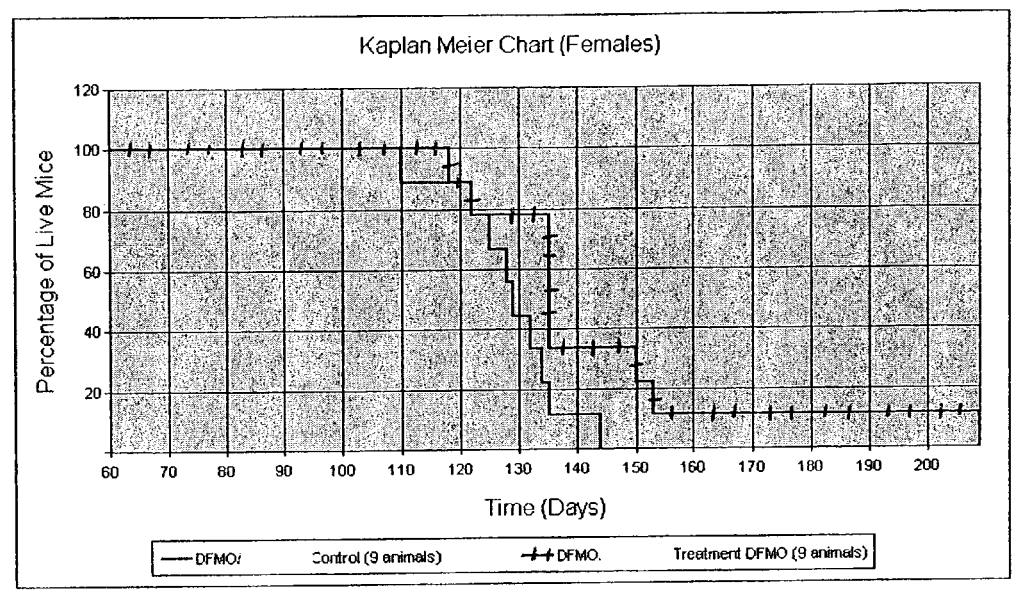
8B.
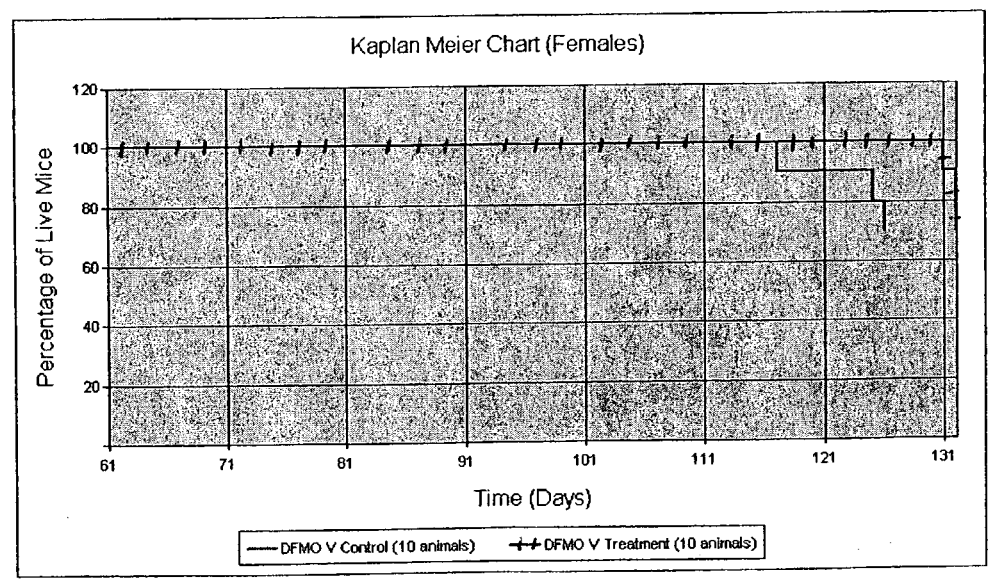

Figure 9A and B.
9A.
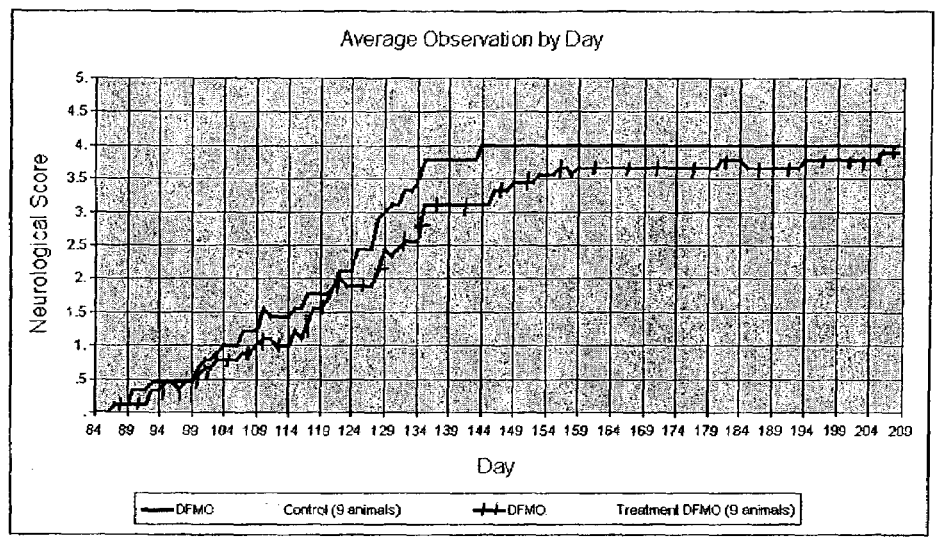
9B.
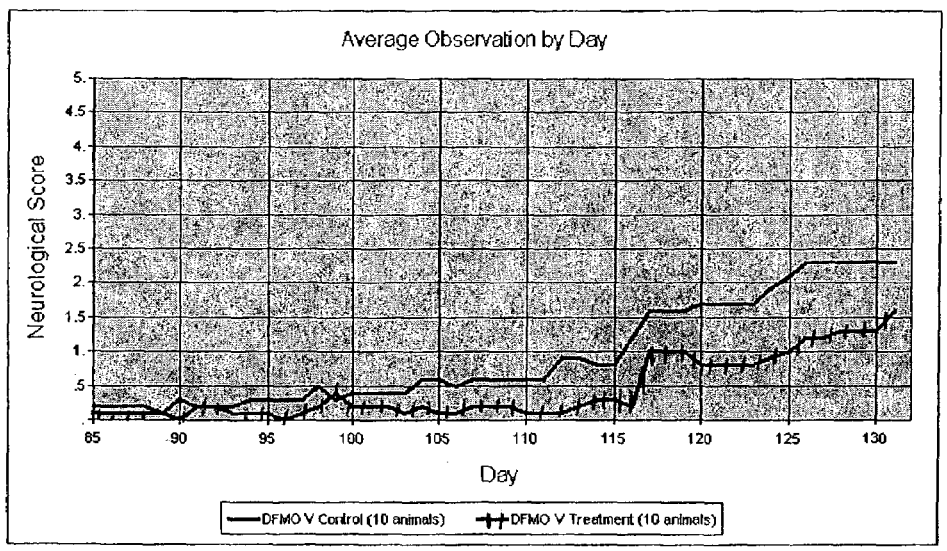

TREATMENT OF NEURODEGENERATIVE DISORDERS THROUGH THE MODULATION OF THE POLYAMINE PATHWAY

RELATED APPLICATIONS

This application claims priority to provisional application U.S. Ser. No. 60/333,263, filed Nov. 16, 2001 entitled "Methods for Monitoring and Treating Amyotrophic Lateral Sclerosis".

BACKGROUND OF THE INVENTION

The technical field of the invention concerns methods and compositions for the treatment of neurodegenerative diseases, such as Amyotrophic Lateral Sclerosis (ALS).

Neurodegenerative diseases are generally characterized by a degeneration of neurons in either the brain or the nervous system of an individual. In addition to ALS, various other diseases, such as Huntington's disease, Parkinson's disease, Alzheimer's disease and Multiple Sclerosis, fall within this category. These diseases are debilitating and the damage that they cause is often irreversible. Moreover, in the case of a number of these diseases, the outcome is invariably fatal.

Progress is being made on many fronts to find agents that can arrest the progress of these diseases. Nonetheless, the present therapies for most, if not all, of these diseases provide very little relief.

Accordingly, a need exists to develop therapies that can alter the course of neurodegenerative diseases or, in the case of diseases like ALS, prolong the survival time of patients with such diseases. More generally, a need exists for better methods and compositions for the treatment of neurodegenerative diseases in order to improve the quality of the lives of those afflicted by such diseases.

SUMMARY OF INVENTION

The present invention provides methods and compositions for modulating polyamine pathway activity as a means for ameliorating neurodegenarative disorders, in particular, for ameliorating the symptoms or onset of amyotrophic lateral sclerosis (ALS). ALS has been associated with increased polyamine levels. In particular, the invention provides an approach to circumvent the present limitations of ALS therapy by modulating the gene and protein products involved the polyamine pathway. For example, by modifying the level of polyamines such as putresceine, by inhibiting the enzyme ornithine decarboxylase (ODC). Other polyamines that are involved in the polyamine pathway that can be modulated include, but are not limited to spermidine, and spermine. The methods and compositions of the invention alter polyamine concentrations or levels such that the alteration provides a protective effect in a subject with ALS. This protective effect manifests in the increase in longevity of the subject, as well as to slow or arrest the progress of the disease.

The proteasome is the biological machinery that is responsible for normal degradation of proteins is also involved in the polyamine pathway. The proteasome damage associated with neurological disorders may lead to an increased half life of ornithine decarboxylase (ODC), the enzyme that converts ornithine into the polymamine putrescine. This increase in ODC yields an increased amount of putrescine and subsequently increased levels of spermine and spermidine. Compositions and methods are disclosed for inhibiting the polyamine pathway producing lower polyamine levels resulting in a beneficial effect on ALS. This can be accomplished by using modulating agents based analogs, or polyamine analogs, that can be used to inhibit the pathway. Substrate mimics of putrescine, spermidine, and spermine would act by blocking the polyamine pathway resulting in downregulation of the pathway, producing decreased levels of polyamines. At least one of the enzymes of the polyamine pathway should be inhibited. The enzyme inhibition may be reversible or nonreversible. In a preferred embodiment, ornithine decarboxylase (ODC) is inhibited leading to a reduction in putrescine levels. Alternatively, proliferation of microglia and astrocytes, which has been associated with neurological disorders can be decreased by administering a therapeutically effective amount of an antiproliferative drug, such as hydroxyurea, DFMO, and various polyamine analogs.

Accordingly, in one aspect, the invention provides a method for modulating polyamine pathway activity, or ameliorating progression of amyotrophic lateral sclerosis (ALS) in a subject, comprising administering to the subject a therapeutically effective amount of a modulating agent that modulates at least one enzyme in the polyamine pathway, such that the modulation produces an amelioration in the progression of ALS.

The modulating agent can be a compound that alters at least one step in the polyamine pathway such that the alteration in the polyamine pathway produces an amelioration of ALS and the symptoms of ALS, such as by increasing the life expectancy of the subject. The modulating agents include, but are not limited to, polyamine analogs, inhibitors that target at least one enzyme in the polyamine pathway, and activators of an antizyme.

The modulating agent can be a polyamine analog of formula 1

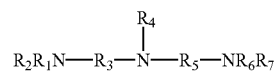

wherein $R_1$, $R_2$, $R_4$, $R_6$ and $R_7$ are independently selected from the group consisting of hydrogen, alkyl and aryl; and $R_3$ and $R_5$ are alkyl groups.

The modulating agent can be a polyamine analog of formula 2.

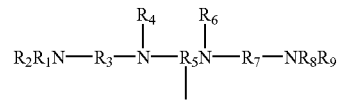

wherein $R_1$, $R_2$, $R_4$, $R_6$, $R_8$, and $R_9$ are independently selected from the group consisting of hydrogen, alkyl and aryl; and $R_3$, $R_5$, and $R_7$ are alkyl groups.

The modulating agent can be a polyamine analog of formula 3.

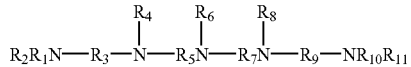

wherein $R_1$, $R_2$, $R_4$, $R_6$, $R_8$, $R_{10}$ and $R_{11}$ are independently selected from the group consisting of hydrogen, alkyl and aryl; and $R_3$, $R_5$, $R_7$ and $R_9$ are alkyl groups.

The modulating agent can be a polyamine analog of formula 4.

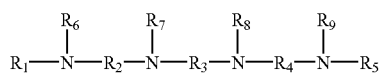

4 wherein $R_1$ and $R_5$ are independently selected from the group consisting of methyl, ethyl, n-propyl, and isopropyl; $R_2$, $R_3$, and $R_4$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl; and $R_6$, $R_7$, $R_8$ and $R_9$ are independently selected from the group consisting of H, methyl, and ethyl.

The modulating agent can be a polyamine analog of formula 5.

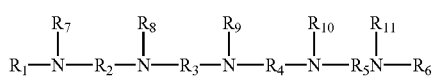

5 wherein $R_1$ and $R_6$ are independently selected from the group consisting of methyl, ethyl, n-propyl, and isopropyl; $R_2$, $R_3$, $R_4$ and $R_5$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl; and $R_7$, $R_8$, $R_9$, $R_{10}$ and $R_{11}$ are independently selected from the group consisting of H, methyl, and ethyl.

The modulating agent can be a polyamine analog of formula 6.

6 wherein $R_4$ is $C_2$–$C_6$ n-alkenyl, $C_3$–$C_6$ cycloalkyl, $C_3$–$C_6$ cycloalkenyl, or $C_3$–$C_6$ aryl; $R_3$ and $R_5$ are independently chosen from a single bond, $C_1$–$C_6$ alkyl, or $C_1$–$C_6$ alkenyl; $R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl; $R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

The modulating agent can be a polyamine analog of formula 7.

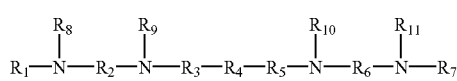

7 wherein $R_4$ is $C_1$–$C_6$ n-alkyl or $C_1$–$C_6$ branched alkyl; $R_3$ and $R_5$ are independently chosen from a single bond or $C_1$–$C_6$ alkyl; $R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl; $R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

The modulating agent can be a polyamine analog selected from the group consisting of 1,11-bis(ethyl)norspermine (1,11-bis(ethylamino)-4,8-diazaundecane), 1,8-bis(ethyl) spermindine, 1,12-bis(ethyl)spermine, 1,14-bis(ethylamino)-5,10-diazatetradecane and 1,19-bis(ethylamino)-5,10,15-triazanonadecane.

In another embodiment, the modulating agent is an ornithine decarboxylase (ODC) inhibitor. The ornithine decarboxylase (ODC) inhibitors include, but are not limited to, difuoromethylornithine (DFMO), α-halomethyl ornithine, methyl ester of monofluoromethyl dehydroornithine, ethyl ester of monofluoromethyl dehydroornithine, and R, R-isomer of methyl acetylenic putrescine.

In yet another embodiment, the modulating agent is hydroxyurea. These modulating agents can be administered as a pharmaceutical composition, and delivered via any appropriate route, such as an oral route and an intravenous route.

The methods and compositions of the invention may also be used to detect if a subject has ALS based on the difference in polyamine levels in test sample from a subject compared with a control sample. Accordingly, in another aspect, the invention pertains to methods for detecting amyotrophic lateral sclerosis (ALS), or monitoring the progression of ALS in a subject by measuring a polyamine level in a first sample from a subject, measuring the polyamine level in a second sample; and comparing the difference in the level of the polyamine in the first and second samples, wherein a difference in the level of the polyamine is an indicator for ALS.

To test whether the subject has ALS, the first sample can be a test sample from a subject, and the second sample can be control sample with normal levels of the polyamine. The difference or deviation in the polyamine levels between the test sample and the control sample indicates that a person has ALS. For example, increased levels of the polyamine, putresciene although a difference in the level of any polyamine involved in the polyamine pathway may be used in the assay, such as a difference in the level of spermidine and spermine.

The assay can also be used to screen for the progression of ALS by monitoring the difference in polyamine levels at different time points in a subject with ALS. This can be accomplished for example, by activating astrocytes to proliferation, adding a pharmacological agent, and monitoring the rate of astrocyte proliferation. Pharmacological agents that inhibit microglia and/or astrocyte proliferation may be useful candidates for further testing in vivo.

Accordingly, in one aspect, the invention pertains to a method to screen for the progression of ALS by monitoring the difference in polyamine levels at different time points in a subject with ALS. This can be performed by taking sample from a subject, or testing phamacological agents in vitro with neurological cell lines. When the first sample is a sample from a subject taken at a first time point, and the second sample is sample from a subject taken at a second time point. The second time point canoe a day, a week, a month, and so forth, until a compendium of data is available with the different levels of the polyamine to monitor the progression of ALS. Also within the scope of the invention, is an assay that measures more than one polyamine, for example, the levels of putresceine and/or spermidine or spermine.

The level of polyamine can be assessed by measuring the expression, or the activity of at least one of the enzymes involved in the polyamine pathways, these include, but are not limited to, ornithine decarboxylase, S-adenosylmethionine decarboxylase, and arginase. Alternatively, the level of polyamine is assessed by measuring the expression or activity of polyamine itself.

In yet another aspect, the invention pertains to a method for screening for a pharmacological agent that modulates the polyamine pathway in a subject with amyotrophic lateral sclerosis (ALS). This assay can be performed by measuring a level of a polyamine in a sample from a subject at a first point, administering a test pharmacological agent to a subject, monitoring the level of the polyamine in a sample from a subject at discrete times points following administration, and comparing the difference in the level of the polyamine to determine if the pharmacological agent changes the level of the polyamine. The polyamine to be measured includes, but is not limited to, putrescine, spermidine, and spermine. Alternatively, more than one polyamine can be detected.

BRIEF DESCRIPTION OF THE DRAWINGS

FIGS. 4A and B are graphs showing repeat studies on the effect of continuous DFMO delivery on survival of a combined group of female and male SOD1 G93A mice;

FIG. 5A and B are graphs of repeat studies showing the effect of continuous DFMO delivery on the neurological progression of a combined group of female and male SOD1 G93A mice;

FIGS. 6A and B are graphs of repeat studies showing the effect of continuous DFMO delivery on survival of male SOD1 G93A mice;

FIGS. 7A and B are graphs of repeat studies showing the effect of continuous DFMO delivery on the neurological progression of male SOD1 G93A mice;

FIGS. 8A and B are graphs of repeat studies showing the effect of continuous DFMO delivery on survival of female SOD1 G93A mice;

FIGS. 9A and B are graphs of repeat studies showing the effect of continuous DFMO delivery on the neurological progression of female SOD1 G93A mice;

DETAILED DESCRIPTION

Figure 1:
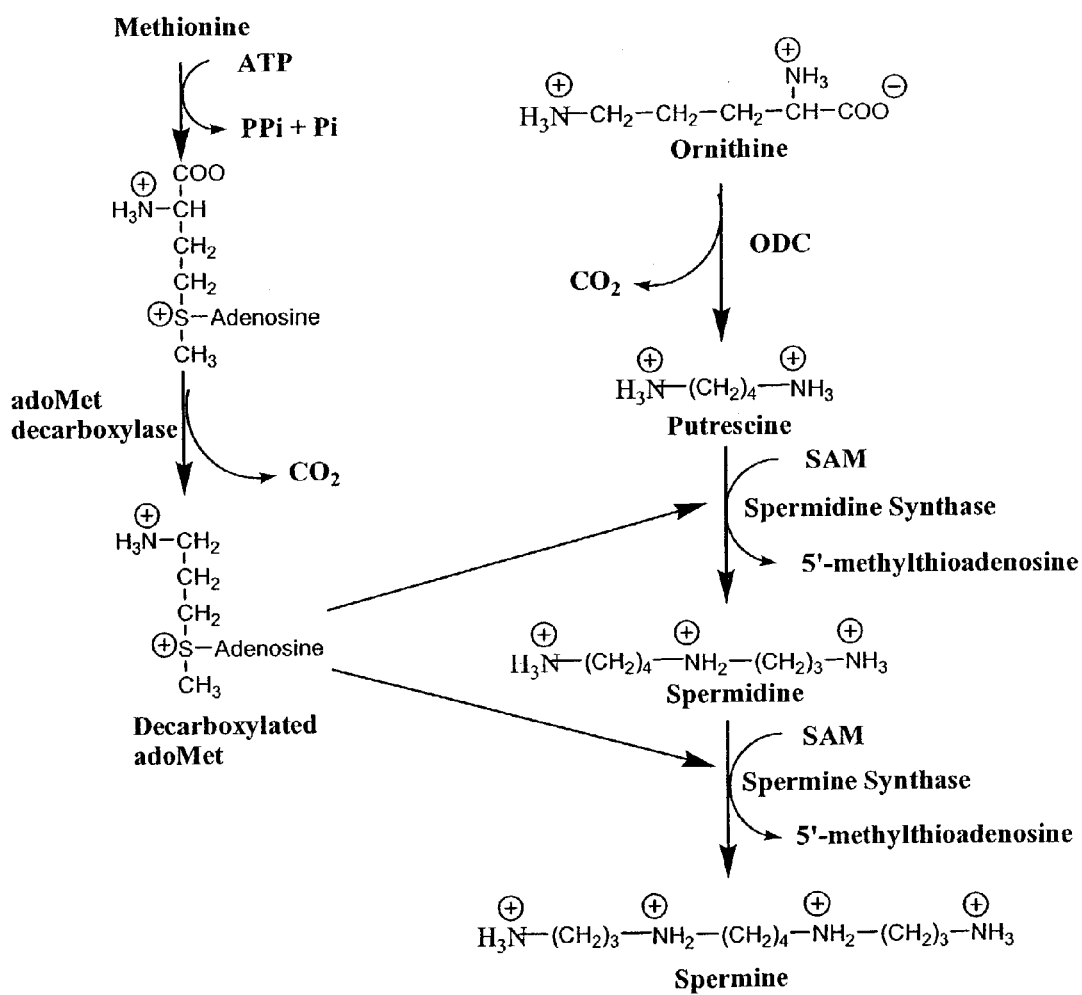
FIG. 1 is a scheme depicting the polyamine pathway.

So that the invention is more clearly understood, the following terms are defined:

The terms "neurological disorder" and "neurodegenerative disorder," as used interchangeably herein refer to an impairment or absence of a normal neurological function or presence of an abnormal neurological function in a subject. For example, neurological disorders can be the result of disease, injury, and/or aging. As used herein, neurological disorder also includes neurodegeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, Amyotrophic Lateral Sclerosis (ALS), multiple sclerosis, Huntington's disease, Parkinson's disease, and Alzheimer's disease.

"Amyotrophic lateral sclerosis" or "ALS" are terms understood in the art and as used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "subject," as used herein, refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "pharmacological agent," as used herein, refers to the compound, or compounds, that are used to modulate polyamine levels, astrocyte, microglia and/or macrophage proliferation in a subject afflicted with a neurodegenerative disease. Exemplary pharmacological agents according to the present invention are the compounds DFMO, hydroxyurea, and DENSPM. Other pharmacological agents include analogs and variants of the compound DFMO, as well as all intermediate compounds and intermediate processes in the creation the compound DFMO. The term "pharmacological agent" is also intended to include other ODC inhibitors as well as inhibitor and analogs of the polyamine pathway. Non-limiting examples of irreversible ODC inhibitors include DFMO, α-difluoromethyl ornithine, α-halomethyl ornithine, methyl and ethyl esters of monofluoromethyl dehydroornithine, the R, R-isomer of methyl acetylenic putrescine (i.e., (2R, 5R)-6-heptyne-2,5-diamine), optical isomers and combinations thereof. In addition, pharmacological agents is also intended to include other ODC inhibitors with similar formula and function to DFMO that are described by the core formulas:

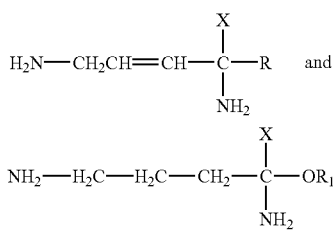

where X is —CHF$_2$ or —CH$_2$F, R is H or COR$_1$, R$_1$ is OH or lower alkoxy groups, and the pharmaceutical acceptable salts and isomers thereof. Other inhibitors of ODC known in the art are described in U.S. Pat. No. 4,499,072, U.S. Pat. No. 5,002,879; and the work of Bey et al. ("Inhibition of Basic Amino Acid Decarboxylases Involved in Polyamine Biosynthesis," Inhibition of Metabolism Biological Significance and Basis for New Therapies, McCann et al, eds.; Academic Press, (1987) 1–32).

The terms "DFMO," and "Eflornithine" are used interchangeably and refer to the compound that is chemically designated as 2-(Difuoromethyl)-DL-ornithine, 2-(Difluoromethyl)ornithine, DL-α-difluoromethylornithine, N-Difluoromethylornithine, ornidyl, and α,δ-Diamino-α-(difluoromethyl)valeric acid, has a molecular formula of C$_6$H$_{12}$F$_2$N$_2$O$_2$, has a molecular weight of 182.17, and has the following chemical structure:

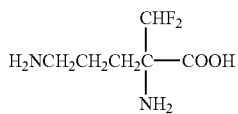

The term "DFMO" is intended to cover all isotopes of the above compound. DFMO is intended to cover all pharmaceutically acceptable salts and/or isomeric forms. Optically pure preparations of α-difluoromethylornithine, having either the (D)-configuration around the alpha carbon of the molecule or the (L)-configuration around the alpha carbon, as well as racemic mixtures are encompassed by the term "DFMO." Racemic and optically pure forms of DFMO can be prepared according to known methods described in U.S. Pat. Nos. 4,413,141, 4,399,151, 4,438,270, 4,560,795, 4,743,691 4,866,206, EP 357029 AZ which are hereby incorporated by reference. The steady state plasma concentration of DFMO can be determined using methods known in the art as described in U.S. Pat. No. 6,277,411, Smithers (*Pharm. Res.* 5, 684–686 (1988)); Bitonti et al. (*Biochem. Pharmacol.* 35, 351–354 (1986)); and Grove et al. (*J. Chromatogr.* 223, 409–416 (1981)) which are hereby incorporated by reference.

The term "polyamine", is a well-understood term of art, and refers to any group of aliphatic, straight-chain amines derived biosynthetically from amino acids; polyamines are reviewed in Marton et al. (*Ann. Rev. Pharm. Toxicol.* 35:55–91 (1995)). By "polyamine" is generally meant a naturally-occurring polyamine or natural polyamine, which are naturally produced in cukaryotic cells. Examples of polyamines include putrescine, spermidine, spermine and cadaverine.

The term "polyamine analog," as used herein, refers to an organic action structurally similar but non-identical to naturally-occurring polyamines such as spermine and/or spermidine and their diamine precursor, putrescine. Polyamine analogs can be branched or unbranched, or incorporate cyclic moieties. Examples of polyamine analogs include, without limitation, N$^1$, N$^{14}$-diethylhomo-spermine (DEHSPM) and N$^1$, N$^{12}$-diethylspermine (DESPM). See, for example, WO 98/17624 and U.S. Pat. No. 5,541,320. U.S. Pat. Nos. 5,037,846 and 5,242,947 disclose polyamines comprising primary amino groups. In some embodiments, polyamine analogs include those wherein all nitrogen atoms of said polyamine analogs are independently secondary, tertiary, or quarternary amino groups.

The term "DENSPM," as used herein, refers to the compound, or compounds, that is chemically designated as 1,3-Propanediamine, N,N'-bis(3-(ethylamino)propyl)- or N(1),N(11)-diethylnorspermine, has a molecular formula of C$_{13}$H$_{32}$N$_4$, and has the following chemical structure:

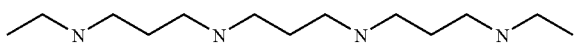

The term "DENSPM" is intended to cover all isotopes and metabolites of the above compound. DENSPM is intended to cover all pharmaceutically acceptable salts and/or isomeric forms as well as structurally similar compounds. Non-limiting examples of derivatives can be found in U.S. Pat. Nos. 5,962,533, 5,886,051, 6,184,232, 6,342,534, and 6,235,794.

The term "alkyl" as used herein refers to a cyclic, branched, or straight chain chemical group containing carbon and hydrogen, such as methyl, butyl, t-butyl, pentyl, cyclopropyl, and octyl. Alkyl groups can be either unsubstituted or substituted with one or more subsituents, e.g., halogen, alkoxy, acyloxy, amino, hydroxyl, mercapto, carboxy, benzyl. Alkyl groups can be saturated or unsaturated (e.g., containing —C═C— or —C C— subunits), at one or several positions. Unless otherwise specified, alkyl groups will comprise 1 to 8 carbon atoms, preferably 1 to 6, and more preferably 1 to 4 carbon atoms. "Cycloalkyl" refers to cyclic alkyl groups only, such as cyclopropyl, cyclobutyl, cyclopentyl, etc. "n-alkyl" refers to a linear (i.e., straight-chain) alkyl group only, while "branched alkyl" refers to branched alkyl groups to the exclusion of cyclic and linear alkyl groups. "Alkenyl" refers to a cyclic, branched, or straight chain chemical group containing carbon and hydrogen where at least one bond is monounsaturated, such as ethenyl, cyclopentenyl, or 1,3-butadienyl. Alkenyl groups can be substituted as indicated for alkyl groups. Alkenyl groups can be designated as cyclic, linear (n-alkenyl) or branched in an analogous fashion to the preceding designations for alkyl. An "aryl" is an unsaturated aromatic carbocyclic group having a single ring (e.g., phenyl), or multiple condensed rings (e.g., naphthyl), which can optionally be unsubstituted or substituted with amino, hydroxyl, alkyl, alkoxy, chloro, halo, mercapto and other substituents.

The term "stereoisomer" as used herein refers to an optical isomer of a compound, including enantiomers and diastereomers. Unless otherwise indicated, structural formula of compounds are intended to embrace all possible sterioisomers.

The term "salt" as used herein refers to a compound formed by the replacement of one or more hydrogen atoms with elements or groups, which is composed of anions and cations, which usually ionizes in water; a salt is formed, for instance, by neutralization of an acid by a base. A polyamine analog salt can comprise, for example, chloride ions.

The phrase "protected derivative" as used herein refers to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) *Protective Groups in Organic Synthesis*, $2^{nd}$ Ed. (John Wiley & Sons, Inc., New York). Exemplary protecting groups for the amino functionality include, but are not limited to, mesitylenesulfonyl (MesSO2), benzyloxycarbonyl (CBz), t-butyloxycarbonyl (Boc), t-butyldimethylsilyl (TBDIMS), 9-fluroenylmethyloxycaronyl (Fmoc), or suitable photolabile protecting groups such as 6-nitroveratryloxy carbonyl (Nvoc).

The term "modulating agent" as used herein refers to a compound that alters at least one step in the polyamine pathway such that the alteration in the polyamine pathway produces a modification in the a neurodegenerative disorder. In particular, the alteration in the polyamine pathway produces an amelioration of ALS and the symptoms of ALS, such as increasing the life expectancy of the subject. The term "modulating agent" includes polyamine analogs, inhibitors that target at least one enzyme in the polyamine pathway, and activators of an antizyme. In one embodiment, the modulating agent targets a specific enzyme involved in the pathway, for example, a modulating agent that interferes with one of the enzymes involved in that pathway such as ODC. The modulation to the pathway can be in the form of increasing, decreasing, elevation, or depressing processes or signal transduction cascades, involving a target gene or a target protein, e.g., ODC. This modulation may result by direct, (e.g., direct binding) or indirect (e.g., use of analogs that mimic the action of the native substrate or bind to the enzyme substrate complex) interaction with the target protein. The modifications can result in a direct affect on the target protein, e.g., inhibition of ODC. Alternatively, the modifications can be indirect modification of a process or cascade involving the target protein, e.g., inhibition of ODC which reduces the concentration of putrescine, which subsequently alters the concentration of spermidine and spermine.

Examples of modulating agents that target specific enzymes include, but are not limited to, ODC inhibitors and polyamine analogs. Examples of ODC inhibitors include, but are not limited to, ornithine decarboxylase (ODC) inhibitor is selected from the group consisting of difuoromethylornithine (DFMO), α-halomethyl ornithine, methyl ester of monofluoromethyl dehydroornithine, ethyl ester of monofluoromethyl dehydroornithine, and R, R-isomer of methyl acetylenic putrescine. Examples of polyamine analogs include, but are not limited to, selected from the group consisting of 1,11-bis(ethyl)norspermine (1,11-bis(ethylamino)-4,8-diazaundecane), 1,8-bis(ethyl)spermindine, 1,12-bis(ethyl)spermine, 1,14-bis(ethylamino)-5,10-diazatetradecane and 1,19-bis(ethylamino)-5,10,15-triazanonadecane. In another embodiment, the modulating agent targets more that one step in the polyamine synthesis, such as an agent that effects both ODC and spermidine synthase or spermine synthase. In another yet another embodiment, more than one modulating agent can be used to alter the polyamine pathway. For example, a combination of modulating agents comprising at least one modulating agent that alters ODC activity and at least one modulating agent that alters spermidine synthase activity or spermine synthase activity. In yet another embodiment, the combination of modulating agents can comprise at least one modulating agent that is a polyamine analog, and at least one modulating agent that is an inhibitor of an enzyme sinvolved in the polyamine pathway.

Examples of the amelioration of the symptoms of ALS in a subject include, but are not limited to, prolonging the life expectancy of a subject, prevention of onset of the disease, slowing or arresting disease progression (as measured by neurological examination or other means, such as MRI, FVC, MUNE etc.), altering the state of microglia and astrocytes in a subject with ALS, improving muscle weakness in a subject, (e.g., improving weakness in the hands, arms, legs), improving swallowing or breathing, improving twitching (fasciculation) and cramping of muscles, improving the use of the limbs in a subject.

The term "therapeutically effective amount" refers to an amount effective, at dosages and for periods of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The term "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The invention is described in more detail in the following subsections:

I. Neurodegenerative Diseases

Regional alterations in polyamines and polyamine metabolism are noted in many neurodegenerative diseases such as Creutzfelt Jacob's (CJD), Huntington's (HD), Stroke and Alzheimer's disease (AD). In addition, over expression of ornithine decarboxylase (ODC) had been observed under basal conditions in the Wobbler mouse, one of the animal models of ALS. Human ALS patients show elevated levels of ornithine (the polyamine precursor) in the spinal tissue and arginase (the enzyme which converts arginine to ornithine) in the cerebrospinal fluid (CSF). Polyamine dysregulation may be the cause of many neurodegenerative conditions, some of which are described below:

(a) Huntington's Disease

Huntington's disease is a hereditary disorder caused by the degeneration of neurons in certain areas of the brain. This degeneration is genetically programmed to occur in certain areas of the brain, including the cells of the basal ganglia, the structures that are responsible for coordinating movement. Within the basal ganglia, Huntington's disease specifically targets nerve cells in the striatum, as well as cells of the cortex, or outer surface of the brain, which control thought, perception and memory. Neuron degeneration due to Huntington's disease can result in uncontrolled movements, loss of intellectual capacity and faculties, and emotional disturbance, such as, for example, mood swings or uncharacteristic irritability or depression.

As discussed above, neuron degeneration due to Huntington's disease is genetically programmed to occur in certain areas of the brain. Studies have shown that Huntington's disease is caused by a genetic defect on chromosome 4, and in particular, people with Huntington's disease have an abnormal repetition of the genetic sequence CAG in the Huntington's disease gene, which has been termed IT15. The IT15 gene is located on the short arm of chromosome 4 and encodes a protein called huntingtin. Exon I of the IT15 gene contains a polymorphic stretch of consecutive glutamine residues, known as the polyglutamine tract (D. Rubinsztein, "Lessons from Animal Models of Huntington's Disease," *TRENDS in Genetics*, 18(4): 202–9 (April 2002)). Asymptomatic individuals typically contain fewer than 35 CAG repeats in the polyglutamine tract.

(b) Multiple Sclerosis

Multiple Sclerosis (MS) is a chronic disease that is characterized by "attacks," during which areas of white matter of the central nervous system, known as plaques, become inflamed. Inflammation of these areas of plaque is followed by destruction of myelin, the fatty substance that forms a sheath or covering that insulates nerve cell fibers in the brain and spinal cord. Myelin facilitates the smooth, high-speed transmission of electrochemical messages between the brain, spinal cord, and the rest of the body. Damage to the myelin sheath can slow or completely block the transmission of these electrochemical messages, which can result in diminished or lost bodily function.

The most common course of Multiple Sclerosis manifests itself as a series of attacks, which are followed by either complete or partial remission, during which the symptoms lessen only to return at some later point in time. This type of MS is commonly referred to as "relapsing-remitting MS." Another form of MS, called "primary-progressive MS," is characterized by a gradual decline into the disease state, with no distinct remissions and only temporary plateaus or minor relief from the symptoms. A third form of MS, known as "secondary-progressive MS," starts as a relapsing-remitting course, but later deteriorates into a primary-progressive course of MS.

The symptoms of MS can be mild or severe, acute or of a long duration, and may appear in various combinations. These symptoms can include vision problems such as blurred or double vision, red-green color distortion, or even blindness in one eye, muscle weakness in the extremities, coordination and balance problems, muscle spasticity, muscle fatigue, paresthesias, fleeting abnormal sensory feelings such as numbness, prickling, or "pins and needles" sensations, and in the worst cases, partial or complete paralysis. About half of the people suffering from MS also experience cognitive impairments, such as for example, poor concentration, attention, memory and/or judgment. These cognitive symptoms occur when lesions develop in those areas of the brain that are responsible for information processing.

(c) Alzheimer's Disease

Alzheimer's disease is a progressive, neurodegenerative disease that affects the portions of the brain that control thought, memory and language. This disease is characterized by progressive dementia that eventually results in substantial impairment of both cognition and behavior. The disease manifests itself by the presence of abnormal extracellular protein deposits in brain tissue, known as "amyloid plaques," and tangled bundles of fibers accumulated within the neurons, known as "neurofibrillary tangles," and by the loss of neuronal cells. The areas of the brain affected by Alzheimer's disease can vary, but the areas most commonly affected include the association cortical and limbic regions. Symptoms of Alzheimer's disease include memory loss, deterioration of language skills, impaired visuospatial skills, and impaired judgment, yet those suffering from Alzheimer's retain motor function.

(d) Parkinson's Disease

Parkinson's disease is a motor system disorder caused by the loss of nerve cells, or neurons, found in the substantia nigra region of the mid-brain. These neurons produce dopamine, a chemical messenger molecule that is found in the brain and helps control or direct muscle activity. Dopamine is used by the cells of the substantia nigra as a neurotransmitter to signal other nerve cells. Parkinson's disease occurs when these neurons die or become impaired, thereby decreasing dopamine levels within the brain. Loss of dopamine causes the neurons to fire uncontrollably, which leaves patients unable to direct or control their bodily movement in a normal manner. The four main symptoms of Parkinson's disease are trembling in the hands, arms, legs, jaw and face; stiffness of the limbs and/or trunk; a slowness of movement, referred to as bradykinesia; and impaired balance and/or coordination. Parkinson's disease is both chronic, i.e., it persists over a long period of time, and progressive, i.e., the symptoms grow worse over time.

(e) Amyotrophic Lateral Sclerosis

Amyotrophic Lateral Sclerosis (ALS) is a universally fatal neurodegenerative condition in which patients progressively lose all motor function—unable to walk, speak, or breathe on their own, ALS patients die within two to five years of diagnosis. The incidence of ALS increases substantially in the fifth decade of life. Evidence is accumulating that as a result of the normal aging process the body increasingly loses the ability to adequately degrade mutated or misfolded proteins. The proteasome is the piece of biological machinery responsible for most normal degradation of proteins inside cells. Age related loss of function or change of function of the proteasome is now thought to be at the heart of many neurodegenerative conditions, including Alzheimer's disease, Parkinson's disease, Huntington's disease, and ALS.

Amyotrophic Lateral Sclerosis (ALS), also called Lou Gehrig's disease, is a fatal neurodegenerative disease affecting motor neurons of the cortex, brain stem and spinal cord. (Hirano, A., "Neuropathology of ALS: an overview," *Neurology*, 47(4 Suppl. 2): S63–6 (1996)). Onset of ALS occurs in the fourth or fifth decade of life (median age of onset is 57) and is fatal within two to five years after diagnosis (Williams, D. B. and A. J. Windebank, "Motor neuron disease (amyotrophic lateral sclerosis)," *Mayo Clin. Proc.*, 66(1): 54–82 (1991)). ALS affects approximately 30,000 Americans with nearly 8,000 deaths reported in the US each year. ALS remains one of the most devastating diseases and advances in treatment are desperately needed.

The cardinal feature of ALS is the loss of spinal motor neurons, which causes the muscles and sporadic forms and the familial forms have now been linked to several distinct genetic loci (Deng, H. X., et al., "Two novel SOD1 mutations in patients with familial amyotrophic lateral sclerosis," *Hum. Mol. Genet.*, 4(6): 1113–16 (1995); Siddique, T. and A. Hentati, "Familial amyotrophic lateral sclerosis," *Clin. Neurosci.*, 3(6): 338–47(1995); Siddique, T., et al., "Familial amyotrophic lateral sclerosis," *J. Neural Transm. Suppl.,* 49: 219–33(1997); Ben Hamida, et al., "Hereditary motor system diseases (chronic juvenile amyotrophic lateral sclerosis). Conditions combining a bilateral pyramidal syndrome with limb and bulbar amyotrophy," *Brain,* 113(2): 347–63 (1990); Yang, Y., et al., "The gene encoding alsin, a protein with three guanine-nucleotide exchange factor domains, is mutated in a form of recessive amyotrophic lateral sclerosis," *Nat. Genet.,* 29(2): 160–65 (2001); Hadano, S., et al., "A gene encoding a putative GTPase regulator is mutated in familial amyotrophic lateral sclerosis 2," *Nat. Genet.,* 29(2): 166–73 (2001)). About 15–20% of familial cases are due to mutations in the gene encoding Cu/Zn superoxide dismutase 1 (SOD1) (Siddique, T., et al., "Linkage of a gene causing familial amyotrophic lateral sclerosis to chromosome 21 and evidence of genetic-locus heterogeneity," *N. Engl. J. Med.,* 324(20): 1381–84 (1991); Rosen, D. R., et al., "Mutations in Cu/Zn superoxide dismutase gene are associated with familial amyotrophic lateral sclerosis." Nature, 362(6415): 59–62 (1993)).

Although a great deal is known about the pathology of ALS little is known about the pathogenesis of the sporadic form and about the causative properties of mutant SOD protein in familial ALS (Bruijn, L. I. and D. W. Cleveland, "Mechanisms of selective motor neuron death in ALS: insights from transgenic mouse models of motor neuron disease," *Neuropathol. Appl. Neurobiol.,* 22(5): 373–87 (1996); Bruijn, L. I., et al., "Aggregation and motor neuron toxicity of an ALS-linked SOD1 mutant independent from wild-type SOD1," *Science,* 281(5384): 1851–54 (1998)). Many models have been speculated, including glutamate toxicity, hypoxia, oxidative stress, protein aggregates, neurofilament and mitochondrial dysfunction, however, no model has comprehensively described the disease pathogenesis (Cleveland, D. W., et al., "Toxic mutants in Charcot's sclerosis," *Nature,* 378(6555): 342–43 (1995); Cleveland, D. W., et al., "Mechanisms of selective motor neuron death in transgenic mouse models of motor neuron disease," *Neurology,* 47(4 Suppl. 2): S54–61, discussion S61–2(1996); Cleveland, D. W., "From Charcot to SOD1: mechanisms of selective motor neuron death in ALS," *Neuron,* 24(3): 515–20 (1999); Cleveland, D. W. and J. D. Rothstein, "From Charcot to Lou Gehrig: deciphering selective motor neuron death in ALS," *Nat. Rev. Neurosci.,* 2(11): 806–19 (2001); Couillard-Despres, S., et al., "Protective effect of neurofilament heavy gene overexpression in motor neuron disease induced by mutant superoxide dismutase," *Proc. Natl. Acad. Sci. USA,* 95(16): 9626–30 (1998); Mitsumoto, H., "Riluzole—what is its impact in our treatment and understanding of amyotrophic lateral sclerosis?" *Ann. Pharmacother.,* 31(6): 779–81 (1997); Skene, J. P. and D. W. Cleveland, "Hypoxia and Lou Gehrig," *Nat. Genet.,* 28(2): 107–8 (2001); Williamson, T. L., et al., "Toxicity of ALS-linked SOD1 mutants," *Science,* 288(5465): 399 (2000)).

Amyotrophic lateral sclerosis (ALS), a progressive, degenerative disease of the voluntary motor system, attacks motor neurons in the cortex, brain stem and spinal cord, and the progressive degeneration of these nerve cells often leads to their death (A. Hirano, "Neuropathology of ALS: an overview," *Neurology* 47:4(S2): S63–66 (1996); See e.g., L P Rowland, Merritt's Textbook of Neurology, ed. L P Rowland, Hereditary and acquired motor neuron disease (Philadelphia: Williams and Wilkins, 1995)). As motor neurons die, they lose the ability to stimulate muscle fibers, and consequently, the brain loses the ability to initiate and control muscle movement. In later stages of the disease, patients become totally paralyzed, yet retain their cognitive functioning.

Early symptoms of ALS include increasing muscle weakness, particularly in the arms and legs, and in the muscles associated with speech, swallowing and breathing. Symptoms of weakness and muscle atrophy usually begin asymmetrically and distally in one limb, and then spread within the neuroaxis to involve contiguous groups of motor neurons. Symptoms can begin either in bulbar or limb muscles. Clinical signs of both lower and upper motor neuron involvement are required for a definitive diagnosis of ALS. Respiration is usually affected late in limb onset patients, but occasionally can be an early manifestation in patients with bulbar onset symptoms. ALS is a universally fatal neurodegenerative condition.

Although the etiology of the disease is unknown, the dominant theory is that neuronal cell death in ALS is the result of over-excitement of neuronal cells due to excess extracellular glutamate. Glutamate is a neurotransmitter that is released by glutaminergic neurons, and is taken up into glial cells where it is converted into glutamine by the enzyme glutamine synthetase, glutamine then re-enters the neurons and is hydrolyzed by glutaminase to form glutamate, thus replenishing the neurotransmitter pool. In a normal spinal cord and brain stem, the level of extracellular glutamate is kept at low micromolar levels in the extracellular fluid because glial cells, which function in part to support neurons, use the excitatory amino acid transporter type 2 (EAAT2) protein to absorb glutamate immediately. A deficiency in the normal EAAT2 protein in patients with ALS, was identified as being important in the pathology of the disease (See e.g., Meyer et al., *J. Neurol. Neurosurg. Psychiatry,* 65: 594–596 (1998); Aoki et al., *Ann. Neurol.* 43: 645–653 (1998); Bristol et al., *Ann Neurol.* 39: 676–679 (1996)). One explanation for the reduced levels of EAAT2 is that EAAT2 is spliced aberrantly (Lin et al., *Neuron,* 20: 589–602 (1998)). The aberrant splicing produces a splice variant with a deletion of 45 to 107 amino acids located in the C-terminal region of the EAAT2 protein (Meyer et al., *Neureosci Lett.* 241: 68–70 (1998)). Due to the lack of, or defectiveness of EAAT2, extracellular glutamate accumulates, causing neurons to fire continuously. The accumulation of glutamate has a toxic effect on neuronal cells because continual firing of the neurons leads to early cell death.

Studies by Gurney showed that the TgN (SOD1-G93A) G1H mice, an established animal model for ALS drug screening, showed significantly increased numbers of activated astrocytes ($P<0.01$) at 100 days of age in both the cervical and lumbar spinal cord regions (Hall E D, O. J., Gurney M E., "Relationship of microglial and astrocytic activation to disease onset and progression in a transgenic model of familial ALS," *Glia,* 23(3): 249–256 (1998)). However, at 120 days of age, the activation lost statistical significance. In contrast, microglial activation was significantly increased several-fold at both 100 and 120 days. Gene expression analysis of post mortem ALS spinal cord demonstrated significant increase in macrophage/microglial activation markers as compared to normal and other disease controls (Malaspina A, et al., "Differential expression of 14 genes in amyotrophic lateral sclerosis spinal cord detected using gridded cDNA arrays," *J. Neurochem.,* 77(1): 132–45 (2001); Gullans, "Gene expression profiling in human ALS spinal cord," 2000). In addition, recent studies based on gene expression analysis of mSOD1 mouse spinal cord at various stages of ALS demonstrated the presence of activated microglial signature well before clinical changes (70 days) suggesting that microglial activation occur prior to neuronal damage (Rothstein, J., "Gene expression profiling in mSOD G93A mice," 2000; Olsen, M. K., et al., "Disease mechanisms revealed by transcription profiling in SOD1-G93A transgenic mouse spinal cord," *Ann. Neurol.*, 50(6): 730–40 (2001)). Therapies used for relapsing multiple sclerosis (MS), including interferon (IFN) beta-1b, IFN beta-1a, and glatiramer acetate (Dhib-Jalbut S. "Mechanisms of action of interferons and glatiramer acetate in multiple sclerosis." *Neurology* (2002) 58(8 Suppl 4):S3–9) may also be useful in combination therapy for ALS. In MS therapy, IFNs bind to cell surface-specific receptors, initiating signaling pathways, which end with the secretion of antiviral, antiproliferative, and immunomodulatory gene products. These antiproliferative gene products may have beneficial effects in the treatment of ALS.

Presently, there is no cure for ALS, nor is there a therapy that has been proven effective to prevent or reverse the course of the disease. Several drugs have recently been approved by the Food and Drug Administration (FDA). To date, attempts to treat ALS have involved treating neuronal degeneration with long-chain fatty alcohols which have cytoprotective effects (See U.S. Pat. No. 5,135,956); or with a salt of pyruvic acid (See U.S. Pat. No. 5,395,822); and using a glutamine synthetase to block the glutamate cascade (See U.S. Pat. No. 5,906,976). For example, Riluzole™, a glutamate release inhibitor, has been approved in the U.S. for the treatment of ALS, and appears to extend the life of at least some patients with ALS. However, some reports have indicated that even though Riluzole™ therapy can prolong survival time, it does not appear to provide an improvement of muscular strength in the patients. Therefore, the effect of Riluzole™ is limited in that the therapy does not modify the quality of life for the patient (Borras-Blasco et al., *Rev. Neurol.*, 27: 1021–1027 (1998)).

(f) Prion-Associated Diseases

The prion protein (PrP) is closely associated with a group of fatal neurodegenerative diseases (Ma, J. and Lindquist, S., "Wild-type PrP and a mutant associated with prion disease are subject to retrograde transport and proteasome degradation," *Proc. Natl. Acad Sci.*, 98(26):14955–14960 (2001)). This group of disorders is characterized by vacuolation of the brain's gray matter, also known as spongioform change. These diseases can take a variety of forms. For example, these diseases can be sporadic, dominantly heritable, as well as transmissible disorders. In humans, the most prevalent form of prion disease is Creutzfeldt-Jakob disease, while in animals, the most common form is known as scrapie. Other disorders in this group include kuru, Gerstmann-Straussler-Scheinker disease and fetal familial insomnia. All disorders are invariably fatal.

In particular, the symptoms of Creutzfeldt-Jakob disease include a rapidly progressive deterioration of intellectual abilities (also known as dementia). The median duration of this illness, from on-set of symptoms to death is around four months. As the disease state progresses, the dementia is typically accompanied by other symptoms such as ataxia, muscular rigidity, and spontaneous and irregular limb jerks, also known as myoclonus.

(g) Spinocerebellar Ataxia

Ataxias are diseases wherein a person loses the ability to coordinate muscle activity during voluntary muscle contraction, and therefore, loses the ability to coordinate smooth bodily movements. Spinocerebellar ataxia is the most common form of hereditary ataxia. Symptoms of the on-set of spinocerebellar ataxia include limb ataxia, nystagmus (rhythmical oscillation of the eyeballs, in either a pendular or jerky motion), kyphoscoliosis (a deformity of the spine characterized by extensive flexion), and pes cavus (a contracted foot, or exaggeration of the normal arch of the foot). The major pathological changes that occur with the disease state occur in the posterior columns of the spinal cord. Spinocerebellar ataxia is most often an autosomal recessive inherited disorder.

(h) Spinomuscular Atrophy

Spinomuscular atrophy (SMA) is a disease of the anterior horn cells of the spinal cord. There are several different types of SMA, including Type I or Acute (Severe) SMA, which is also known as Werdnig-Hoffmann Disease, Type II (Chronic) SMA, Type III (Mild) SMA, often referred to as Kugelberg-Welander or Juvenile SMA, Type IV (Adult Onset) SMA, and Adult Onset X-Linked SMA, also known as Kennedy's Syndrome or Bulbo-Spinal Muscular Atrophy, which occurs in males, but females may be carriers. SMA affects the voluntary muscles that are responsible for activities such as crawling, walking, head and neck control, and swallowing. SMA mainly affects the proximal muscles, or the muscles closes to the trunk of a person's body. Symptoms include weakness in the legs and arms, with weakness in the legs being greater than weakness in the arms. Other symptoms may include tongue fasciculations, or abnormal movements of the tongue. During the course of SMA, however, a person's senses, feelings and intellectual activity remain unaffected.

II. Polyamine Pathway Modulating Pharmacological Agents

Regionally altered polyamine metabolism is noted in many neurodegenerative diseases such as Creutzfelt Jacob's (CJD), Huntington's (HD), Stroke and Alzheimer's disease (AD). The Wobbler mouse, which is used as a motor neuron disease model, has been shown to have, increased spinal expression of ornithine decarboxylase (ODC), the rate-limiting enzyme in polyamine biosynthesis. Ornithine, the substrate of ODC, has been shown to be substantially elevated (300%) in the spinal tissue of human ALS patients. Arginase, the enzyme responsible for the synthesis of ornithine, is over-expressed two to eight fold in the CSF of human patients. The present invention provides methods and assays that relate polyamine dysregulation to neurological disorders such as ALS. In addition, screening assays for pharmacological agents that capable of reducing polyamine dyregulation are provided by the present invention.

(a) The Polyamine Pathway

The polyamines, putrescine, spermidine, and spermine, are a group of multivalent organic cationic cell components present in all living cells. The polyamines play important roles in many fundamental cellular processes including the regulation of cell proliferation, cell differentiation, signaling immune cell activation, transformation, and apoptosis. The majority of signal transduction pathways intersect polyamine biosynthesis pathways and/or those pathways which regulate intracellular polyamine levels. While their exact roles in these processes are still being explored, these processes are putatively related to the unique charge distribution and flexibility of these cationic polyamines. They affect these processes by regulating intracellular signals, chromatin structure, replication, transcription and translation. More recently they are thought to even regulate ion channels. Polyamines can directly bind to DNA and modulate DNA-protein interactions. These functions may be directly related to polyamines' role in cell proliferation as well as cell death. The production of hydrogen peroxide during polyamine catabolism may directly influence cell death (Thomas et al. *Cell. Mol. Life Sci.* 58: 244–258 (2001)). Due to the fundamental role polyamines play in cell function, cells have developed redundant mechanisms for the regulation of polyamines ranging from multiple synthetic pathways to extra cellular uptake mechanisms. The synthesis, uptake, and steady state of the three major polyamines, putrescine, spermidine, and spermine, are tightly regulated at transcriptional, translational and breakdown levels.

Ornithine, derived from the amino acid arginine as part of the urea cycle, is one of the starting materials for polyamine biosynthesis. Putrescine is synthesized from ornithine through the action of the enzyme ornithine decarboxylase (ODC). The higher polyamines, spermidine and spermine, respectively, are produced via the sequential addition of aminopropyl groups from decarboxylated adomet (See FIG. 1) catalyzed by S-adenosyl methionine decarboxylase (SAMDC), spermidine and spermine synthase. Polyamines are found in millimolar concentrations in mammalian cells. The level of polyamines vary between gender (Pegg et al. *Am. J. Physiol.* 243: C212–C221 (1982)).

(b) Modulation of the Polyamine Pathway

Polyamine dysregulation is observed in a variety of diseases. Ornithine decarboxylase, the rate-limiting enzyme in polyamine metabolism is regulated transcriptionally and post-translationally. Post-translational stability of ODC is regulated by the 26S proteasome through regulated degradation of ODC by antizyme. ODC is also a unique protein, which is not degraded through the ubiquitination pathway that occurs in the degradation of most proteins. Proteasomal dysfunction is implicated in many of the neurodegenerative diseases described above and in ALS. Studies in yeast have shown that proteasomal mutants show an increased half-life of ODC as compared to wild-type cells. This suggests that proteasomal dysfunction can increase ODC half-life and increase the polyamine pool in defective cells. Amplification or up regulation of ODC is observed during carcinogenic events and in hyperproliferative diseases. ODC is under expressed in inflammatory Crohn's disease. Polyamine inhibition is beneficial in some autoimmune systemic lupus erythematosus (SLE) disease and inflammation models. Inhibitors of polyamine biosynthesis, polyamine analogs, and oligonucleotide/polyamine analog combinations have been shown have a positive effect in the reduction, treatment, and prevention of cancer.

Polyamines are regulated at several levels including synthesis, degradation, uptake and efflux. Modification of polyamine levels at any one of these levels, such that neurological disorders are affected, is within the scope of the present invention. The rapid turnover rate of ODC is positively regulated by polyamines. Additionally cells have a transport mechanism to uptake exogenous polyamines. ODC, S-adenosyl methionine decarboxylase (SAMDC), and spermidine/spermine acetyl transferase (SSAT) may be regulated externally at the transcription level and may be regulated by polyamines at the translation level. Altering an interacting signal transduction pathway may be capable of decreasing the level of polyamines ultimately decreasing neurological disorders and hence are within the scope of the present invention.

Polyamine levels are also tightly regulated by a complex of product feedback systems. ODC is sensitive to slight changes in spermidine and spermine levels, but is relatively insensitive to its immediate product putrescine (Hayashi et al. *Biochem* 306: 1–10 (1995); (Mitchell et al. *Biochim. Biophys. Acta* 840: 309–316 (1985)). As little as 50 µM spermidine in the culture medium can inhibit ODC production for hours. The present invention associates high levels of putrescine with neurological disorders. Thus, one embodiment involves the use of spermidine or spermidine analogs which are capable of negatively regulating ODC as discussed below.

The increase in ODC activity may be related to decreased proteasomal function. Proteasomal activity decreases with age. Conversely ODC activity increases with age. The average age of ALS onset is 55 years of age. Considering the declining proteasomal function concurrent with increased ODC activity in aging, a causative relationship may exist between proteasome alteration and ODC stabilization. This relationship may be exploited leading to new therapies for neurological disorders.

Ornithine decarboxylase (ODC), the rate limiting step in the biosynthesis of polyamines from ornithine, has been shown to be negatively regulated by an antizyme, through a non-ubiquination mediated degradation by the 26S proteasome in an ATP-dependent manner (Murakami et al. *Biochem. J.* 304: 183–187 (1993)). The 26S proteasome irreversibly inactivates ODC, possibly through unfolding, prior to its degradation. The level of antizyme (AZ) is regulated translationally by polyamine load through an unusual translational frameshifting process. To date, three antizymes have been discovered that have an effect on polyamine levels (Ivanov et al. *Proc. Natl. Acad. Sci. USA* 97: 4808–4813 (2000)). Degradation of ODC consists of a multistep sequence, including recognition, sequestration, unfolding, translocation, and proteasome mediated degradation. Functional studies (Coffino, P. *Biochimie* 83: 319–23 (2001)) have identified regions of ODC and AZ that are required for ODC degradation. A region on the surface of an alpha-beta barrel forming one domain of the ODC monomer has been shown to be required for AZ binding. The carboxyl-terminal region of ODC, exposed by interaction with AZ, is thought to play a role in ODC recognition by the 26S proteasome ((Murakami Y et al. *Biochem Biophys Res Commun* 267:1–6 (2000)) and (Andreassen et al. *Exp. Neurol.* 168: 419–424 (2001))). While the carboxy-terminal half of AZ is sufficient for binding to ODC, an additional domain located within the AZ amino terminus must be present for stimulation of ODC degradation by the proteasome (Coffino, P. *Biochimie* 83: 319–23 (2001)).

Modification of any of the multiple steps in the sequence leading to ODC degradation may lead to decreased levels of ODC (Mitchell J L et al. *Biochem Soc Trans* 26:591–595 (1998)). By upregulating or increasing the lifetime of at least one of these antizymes, leading to a decrease in ODC and lower levels of polyamines, neurological disorders may be treated and/or reduced. Oligoamine constructs as well as conformationally constrained analogs of the polyamines have been shown to stimulate antizyme synthesis (Mitchell J L et al. *Biochem J* 366: 663–671 (2002)). Polyamine analogs that are capable modulating antizyme production, including but not limited to, bisethylnorspermine, bisethylhomospermine, 1,19-bis-(ethylamino)-5,10,15-triazanonadecane, may used in the treatment of neurological disorders. Furthermore, studies indicate N-methyl-D-aspartate (NMDA) receptors may also play a role in ODC modulation (Reed L J et al. *J Neurochem* 55: 780–787 (1990)).

To study the role of the polyamines and ODC in ALS, polyamine levels can be analyzed in the early and late stage SOD1 G93A mice. In addition, the alterations in other polyamines and ODC in ALS are being investigated. Although increased polyamines are detected in ALS mouse brains, its role in neurodegeneration is not clear. To test the therapeutic implication of this pathway in ALS, the efficacy of polyamine analogs, ornithine analogs, and ODC inhibitors, the SOD1 G93A mice can be screened using the assays provided by the present invention. The ODC inhibitor Eflornithine (DFMO) treated animals show signs of improved survival (See Examples 2 and 3). These data demonstrate a target in ALS that can be exploited for drug development.

Polyamine deregulation in the SOD1 G93A mouse model may be related to alterations in proteasomal activity. Studies in yeast have shown that proteasomal dysfunction can lead to decreased degradation of ODC, changing its half life from a few minutes to a few hours. Proteasome mediated polyamine up regulation could lead not only to proliferation of astrocytes and microglia but could also induce neuronal apoptosis by driving neurons into cell cycle. Additionally polyamines in microglia can induce release of inflammation mediators such as reactive oxygen species (ROS) and pro-inflammatory cytokines.

The basal activity of ornithine decarboxylase (ODC) was found to be higher in the spine of Wobbler mice, a model for neurodegenerative disease, than in control animals (M. Gonzalez Deniselle et al. *J Steroid Biochem Mol Biol.* 60(3–4):205–13 (1997)). This increased ODC activity may be associated with astrocytosis within the spinal cord of the Wobbler mice since ODC activity may originate in astrocytes (Cintra et al. *Neurosci. Lett.* 76: 149–153 (1987)). Wobbler mice also showed intense proliferation of astrocytes immunoreactive (ir) for glial fibrillary acidic protein (GFAP) in grey and white matter of the spinal cord. GFAP-ir astrocytes have also been found in the brains of ALS patients (Murayama et al. *Acta Neuropathol.* (*Berl.*) 82: 456–461 (1991)) Thus, astrocytosis and increased ODC activity may represent the glial and neuronal response which leads to neurodegeneration. In addition, microgliosis and activation of microglia has been seen in neurodegnerative diseases. The observed microgliosis may be related to increased ODC expression which leads to killing of neurons by microglia. The present invention provides methods and compositions for modulating, treating, reducing, and/or slowing neurodegeneration, e.g., ALS, by inhibiting the polyamine pathway and/or cell proliferation. In a preferred embodiment, the polyamine pathway is inhibited through the administration of ODC inhibitors. In another embodiment, microgliosis and/or astrocytosis is inhibited through the administration of ODC inhibitors. In another embodiment, a step in the polyamine pathway can be inhibited to modulate, treat, reduce, and/or slow neurodegeneration, e.g., ALS, through the administration of at least one of the group comprising, polyamine analogs, Adomet analogs, adomet decarboxylase inhibitors (i.e. methylglyoxylbis (guanylhydrazone)), ODC inhibitors, and arginase inhibitors. In yet another embodiment, more than one enzyme in the polyamine pathway can be simultaneously and specifically suppressed resulting in a synergistic effect. Various natural and chemical inhibitors of the polyamine pathway are reported in the literature and described below.

(c) Polyamine Synthesis Inhibitors i) Polyamine Analogs

Compounds that mimic the structure of the polyamines, but inhibit the pathway can be used in the present invention to lower polyamine levels in a subject with a neurological disorder. The polyamine analogs can be designed to alter the polyamine methylene backbone changing the charge distribution of the analog. The charge and length of the methylene bridges between the cations has been showed to be important to the biological function of the polyamines. Thus, these altered polyamine analogs can block the polyamine pathway leading to decreased production. Examples of polyamine analogs are described in U.S. Pat. Nos. 6,235,794 and 6,172,261. Polyamine analogs have also been shown to be effective as antiproliferative agents (Bergeron et al. *J Med Chem* 44(15): 2451–2459 (2001)).

The polyamine analogs used in the present invention include compounds of the formulas 1, 2, 3, 4, and 5, and the corresponding stereoisomers, salts, and protected derivatives thereof:

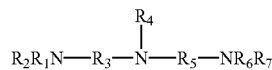

1 where $R_1$, $R_2$, $R_4$, $R_6$ and $R_7$ are independently selected from the group consisting of hydrogen, alkyl and aryl, and where $R_3$ and $R_5$ are alkyl groups;

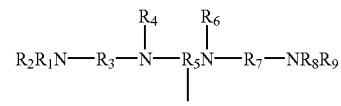

2 where $R_1$, $R_2$, $R_4$, $R_6$, $R_8$, and $R_9$ are independently selected from the group consisting of hydrogen, alkyl and aryl, and where $R_3$, $R_5$, and $R_7$ are alkyl groups;

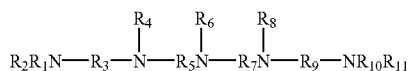

3 where $R_1$, $R_2$, $R_4$, $R_6$, $R_8$, $R_{10}$ and $R_{11}$ are independently selected from the group consisting of hydrogen, alkyl and aryl, and where $R_3$, $R_5$, $R_7$ and $R_9$ are alkyl groups;

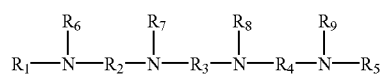

4 where $R_1$ and $R_5$ are independently selected from the group consisting of methyl, ethyl, n-propyl, and isopropyl; where $R_2$, $R_3$, and $R_4$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl; and where $R_6$, $R_7$, $R_8$ and $R_9$ are independently selected from the group consisting of H, methyl, and ethyl;

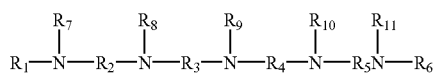

5 where $R_1$ and $R_6$ are independently selected from the group consisting of methyl, ethyl, n-propyl, and isopropyl; where $R_2$, $R_3$, $R_4$ and $R_5$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl; and where $R_7$, $R_8$, $R_9$, $R_{10}$ and $R_{11}$ are independently selected from the group consisting of H, methyl, and ethyl.

In some embodiments, the polyamine analogs will include compounds of the formula 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and further where $R_2$ and $R_{11}$ are hydrogen atoms.

In some embodiments, the polyamine analogs will include compounds of the formula 3, where $R_3$, $R_5$, $R_7$ and $R_9$ are independently $(CH_2)_x$ groups, where x is an integer from 2 to 6, and where $R_4$, $R_6$ and $R_8$ are hydrogen atoms, and where $R_1$ and $R_{10}$ are alkyl groups, and where $R_2$ and $R_{11}$ are hydrogen atoms, and further where the polyamine analogs have a molecular weight less than 500.

In some embodiments, compounds also include compounds of the formula 4, where $R_6$, $R_7$, $R_8$ and $R_9$ are H; where $R_1$ and $R_5$ are ethyl; where $R_6$, $R_7$, $R_8$ and $R_9$ are H and $R_1$ and $R_5$ are ethyl; and/or where $R_2$ and $R_4$ are independently selected from the group consisting of $C_1$–$C_6$ alkyl and $R_3$ is independently selected from the group consisting of $C_1$–$C_6$ alkyl, $C_3$–$C_6$ alkenyl, $C_1$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl.

Additional polyamine analogs useful in the present invention include compounds of the formula 6, and the corresponding stereoisomers, salts, and protected derivatives thereof:

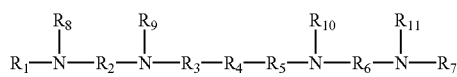

6 where $R_4$ is $C_2$–$C_6$ n-alkenyl, $C_3$–$C_6$ cycloalkyl, $C_3$–$C_6$ cycloalkenyl, or $C_3$–$C_6$ aryl; $R_3$ and $R_5$ are independently chosen from a single bond, $C_1$–$C_6$ alkyl, or $C_1$–$C_6$ alkenyl; $R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl; $R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

In some embodiments of the compounds of formula 6, $R_1$ and $R_7$ are independently chosen from $C_1$–$C_6$ alkyl or $C_2$–$C_6$ alkenyl.

Additional polyamine analogs useful in the present invention include compounds of the formula 7, and the corresponding stereoisomers, salts, and protected derivatives thereof:

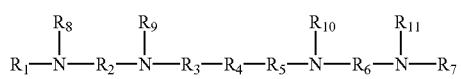

7 where $R_4$ is $C_1$–$C_6$ n-alkyl or $C_1$–$C_6$ branched alkyl; $R_3$ and $R_5$ are independently chosen from a single bond or $C_1$–$C_6$ alkyl; $R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl; $R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

In some embodiments, the compounds of formula 7, $R_1$ and R7 are independently chosen from $C_1$–$C_6$ alkyl or $C_2$–$C_6$ alkenyl, $R_4$ is $C_1$–$C_6$ saturated n-alkyl or $C_1$–$C_6$ saturated branched alkyl, and $R_3$ and $R_6$ are independently chosen from a single bond or $C_1$–$C_6$ saturated n-alkyl.

In some embodiments, all the nitrogens of the polyamine analog are independently secondary, tertiary, or quarternary amino groups.

Among polyamine analogs for use in this invention are those compounds with a demonstrated ability to modulate naturally occurring polyamine levels in cells. Without intending to be limited by theory, possible mechanisms include competition in the polyamine synthesis pathway; upregulation of polyamine catabolizers such as SSAT; affecting polyamine metabolism.

Preferred polyamine analogs include, but are not limited to, 1,11-bis(ethyl)norspermine (1,11-bis(ethylamino)-4,8-diazaundecane; BE-3-3-3); 1,8-bis(ethyl)spermindine (BES); 1,12-bis(ethyl)spermine (BESm; DESPM ($N^1$, $N^{12}$-diethylspermine; SunPharm); 1,14-bis(ethylamino)-5,10-diazatetradecane (BE-4-4-4) (Diethylhomospermine, $N^1$, $N^{14}$-diethylhomospermine; DEHOP or DEHSPM; SunPharm); diethyl-norspermine (DENOP; SunPharm); and 1,19-bis(ethylamino)-5,10,15-triazanonadecane (BE-4-4-4-4).

In addition, polyamine analogs as described in U.S. Pat. Nos. 5,889,061, 5,880,161 and 5,541,230 and in international patent application WO 00/66587 may be used in the present invention.

The polyamine analogs, described above, have been synthesized and screened in a variety of models of disorders such as cancer. Diamines (e.g., derivatives and/or analogs of putrescine with varying numbers of methylene groups in the alkyl chain), triamines (e.g. derivatives and/or analogs of spermidine with varying numbers of methylene groups in the alkyl chain), tetramines (e.g. derivatives and/or analogs of spermine with varying numbers of methylene groups in the alkyl chain), and compounds with five or more amino groups (e.g., not direct derivatives of natural polyamines) can be used in the present invention to modulate neurodegenerative disorders such as ALS.

The role of putrescine derivatives (i.e., the apoptosis inducer ORI-1313) is being explored for their effect on melanoma and leukemia (Porter et al. *Cancer Res.*, 47: 2821–2825(1987)). Through the use of competition experiments with various putrescine analogs, the putrescine and ornithine recognition site on PotE was determined to be located at the cytoplasmic surface and the vestibule of the pore consisting of 12 transmembrane segments. Both uptake and excretion of putrescine are catalyzed by PotE (Kashiwagi, K. et al., *J. Biol. Chem.* 275: 36007–36012 (2000)).

A comparison of the structure-activity relationships between spermidine and spermine analogues showed that activity is highly dependent on the length of the triamines and the size of the N(alpha),N(omega)-substituents. Various triamines (spermidine analogs) may offer therapeutic advantages over the corresponding tetraamines (spermine analogs) (Bergeron et al. *J Med Chem* 40(10):1475–1494 (1997)). Studies using fluorinated spermidine analogs illustrate the different biological and biochemical properties of these analogs. For example, the difluorinated spermidine analogues, 7,7-difluorospermidine, was shown to be capable of repressing ODC and SAM-DC activities, depleting tumor cells of its spermine content, and exerting polyamine antagonist effects (Mamont et al. *Adv Exp Med Biol* 250: 691–706 (1988)).

In addition, Burns et al. describe the synthesis and characterization of spermine/amino acid conjugates which may inhibit the uptake of spermidine into MDA-MB-231 breast cancer cells. One analog, Lys-Spm conjugate, when used in combination with DFMO, was shown to inhibit cytostatic growth of a variety of cancer cells, reduce cellular concentrations of putrescine and spermidine while not affecting the levels of spermine (Burns et al. *J Med Chem* 44(22): 3632–3644 (2001)). In one embodiment of the present invention, the Lys-Spm conjugate analog may be used in combination with DFMO to modulate neurodegenerative disorders, e.g. ALS In another aspect, the invention pertains to using spermine analogs to modify or modulate the polyamine pathway. In a preferred embodiment, the spermine analog is N(1),N(11)-diethylnorspermine (DENSPM). The term "DENSPM" is intended to cover all isotopes and metabolites of the above compound. DENSPM is intended to cover all pharmaceutically acceptable salts and/or isomeric forms as well as structurally similar compounds. Non-limiting examples of derivatives can be found in U.S. Pat. No. 5,962,533, 5,886,051, 6,184,232, 6,342,534, and 6,235,794. DENSPM has been shown to reduce cellular concentrations of putrescine, spermidine and spermine by down-regulating the activity of the polyamine biosynthetic enzymes and up-regulating the activity of the catabolic enzyme spermidine/spermine N(1)-acetyltransferase (SSAT). Studies using DENSPM in the breast cancer cell line L56Br-C1, have linked DENSPM's ability to increase SSAT activity and inhibit of cell proliferation to the activation of caspases. (Hegardt et al. "Rapid caspase-dependent cell death in cultured human breast cancer cells induced by the polyamine analogue N(1),N(11)-diethylnorspermine." *Eur J Biochem* 269(3):1033–9 (2002)). Phase I clinical trial in patients with advanced non-small cell lung cancer suggest that DENSPM can safely be administered to patients with minimal toxicity (Hahm et al. "Phase I study of N(1),N(11)-diethylnorspermine in patients with non-small cell lung cancer." *Clin Cancer Res* 8(3):684–90 (2002)).

Furthermore, Bergeron and co-workers described new synthesis methods for hydroxylated polyamine analogs including N(1)-cyclopropylmethyl-N(11)-ethylnorspermine (CPMENSPM) and the first synthesis of (2R,10S)-N(1)-cyclopropylmethyl-2,10-dihydroxy-N(11)-ethylnorspermine [(2R,10S)-(HO)(2)CPMENSPM]. Bergeron et al. concluded that the hydroxylation of norspermine analogues may be improve antiproliferative activity while reducing toxicity. These cyclopropyl compounds reduced cellular concentrations of putrescine and spermidine. In addition, the cyclopropyl compounds, as well as DENSPM and (2R,10R)-(HO)(2)DENSPM, decrease ornithine decarboxylase and S-adenosylmethionine decarboxylase activity (Bergeron et al. "Synthesis and evaluation of hydroxylated polyamine analogues as antiproliferatives." *J Med Chem* 44(15):2451–9 (2001)). Therefore, DENSPM derivatives as well as modified DENSPM derivatives (i.e. hydroxylated) may be useful in the present invention to reduce neurodegenerative disorders.

In one aspect, the invention pertains to using DFMO to ameliorate the symptoms and onset of ALS. DFMO is an inhibitor of ornithine decarboxylase, which is the rate limiting enzyme of the polyamine biosynthetic pathway. DFMO inhibits polyamine synthesis and has been shown to be effective for cancer prevention in many organ systems, inhibition of cancer growth (U.S. Pat. No. 6,013,646), and reduction of tumor size. DFMO's action is synergistic with other antineoplastic agents. In addition, DFMO has been used as a trypanocidal agent. DFMO has been used both topically and systemically. Topically DFMO, or Vaniqa, has been used to inhibit or slow hair growth. Systemically, DFMO, or Ornidyl, has been used to treat African sleeping sickness, a disease caused by protozoa.

The terms "DFMO," and "eflornithine," as used interchangeably herein, refer to the compound that is chemically designated as 2-(Difuoromethyl)-DL-ornithine, 2-(Difluoromethyl)ornithine, DL-α-difluoromethylornithine, N-Difluoromethylornithine, orndiyl, and α,δ-Diamino-α-(difluoromethyl)valeric acid, has a molecular formula of $C_6H_{12}F_2N_2O_2$, has a molecular weight of 182.17, and has the following chemical structure:

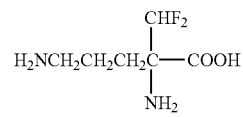

The term "DFMO" is intended to cover all isotopes of the above compound.

Besides the polyamine, spermine or spermidine analogs (collectively referred to as "analogs") listed above, stereoisomers, salts or protected derivatives thereof, can be used. The invention also comprises methods of using an effective amount of any of the analogs listed above, or stereoisomers, salts or protected derivatives thereof (or a composition comprising an effective amount of any of the analogs listed above, or stereoisomers, salts or protected derivatives thereof) in effecting a modulation of the polyamine pathway and ALS. The invention also comprises any analog listed above, or stereoisomers, salts or protected derivatives thereof, for use in preparing compositions (i.e., medicaments) useful for amelioration of ALS.

Any analog listed above, or stereoisomers, salts or protected derivatives thereof (or a composition comprising an effective amount of any polyamine analog listed above, or stereoisomers, salts or protected derivatives thereof) can be used in vitro or in vivo. For in vitro use, a suitable biological sample (such as a blood sample, which may or may not be enriched for the abnormal macrophage population) is contacted with the composition(s). For in vivo use, a composition of the invention is generally administered according to the manufacturer's/supplier's instructions. Generally, the analogs are administered by subcutaneous or intravenous injection. They can also be administered orally.

The amount of an analog (or stereoisomers, salts or protected derivatives thereof) to be administered will depend on several variables, such as the particular analog (or sterioisomer, salt or protective derivative) used, the time course of administration, the condition of the subject, the desired objective, the extent of disease, how many doses will be administered, and whether any other substances are being administered. In the case of polyamine analogs (or stereoisomer, salt, or protected derivative thereof), the amount will generally be between about 1 to about 300 mg/m²/day, possibly between about 15 to about 150 mg/m²/day. Administration is generally intermittent, meaning that analog (or stereoisomer, salt, or protected derivative thereof) is administered at a period of at least 1–2 days and then not administered for a period of at least 1–2 days, with the cycle repeated as indicated. In one embodiment, the polyamine analog (or stereoisomer, salt, or derivative thereof) is administered for 7 days for three weeks, followed by a "a drug holiday" when no analog is administered.

Routes of administration will generally depend on the nature of the particular polyamine analog (or stereoisomer, salt or protective derivative) used, and can be, for example, oral or by injection (subcutaneous or intravenous). Administration is generally by intravenous or subcutaneous injection.

Preferably, an analog (or stereoisomer, salt or protected derivative), or other modulating agent that interferes with the polyamine synthetic pathway, polyamine metabolism, and/or the intracellular concentration maintenance of an polyamine, e.g., putrescine, spermidine, or spermine, is administered in a suitable pharmaceutical excipient. Pharmaceutical excipients are known in the art and are set forth in Remington: *The Science and Practice of Pharmacy*, 20$^{th}$ edition, Mack Publishing (2000). The polyamine analog can also be associated with another substance that facilitates agent delivery to target cell, e.g. macrophages, neurons, microglia, and astrocytes, or increases specificity of the agent to these target cells. For example, an agent(s) can be associated into liposomes as a means of delivery to a target cell. Liposomes are known in the art. The liposomes in turn can be conjugated with targeting substance(s), such as IgGFc receptors. Substances that increase macrophage phagocytosis such as zymosan or tetrachlorodecaoxygen (TCDO) and/or activation such as MCSF, GMCSF or IL-3 may also be used to increase uptake of anti-proliferative agent(s).

A polyamine, spermidine or spermine analog (or stereoisomer, salt or protected derivative) may be administered alone, or in conjunction with other substances and/or therapies, depending on the context of administration (i.e., desired end result, condition of the individual, and indications). The phrase "in conjunction with" means that an agent is administered prior to, concurrently, or after other substance or therapy. Examples of substances that might be administered in conjunction with an agent include, but are not limited to, riluzole (RILUTEK®). Studies with riluzole, approved by the Food and Drug Administration for therapy of ALS, have demonstrated in statistically significant effects on survival of patients with ALS (Bensimon et al. *New Engl. J. Med.* 330:585–591 (1994); Lacomblez et al. *Lancet* 347: 1425–1431 (1996)). Often ALS therapy includes treatment aimed at control of symptoms. Accordingly, examples of substances for treatment of symptoms associated with ALS that might be administered in conjunction with an agent include, but are not limited to, baclofen, diazepam, trihexyphenidyl and/or amitriptyline.

The mechanistic effectiveness of various polyamine, spermidine, or spermine analogs and enzyme inhibitors can be determined in specific cell lines at least in part by their ability to deplete intracellular polyamine pools. Kramer et al. (*Biochem. Pharmacol.* 50:1433 (1995)) describe the use of 4-fluoro-L-ornithine to monitor metabolic flux through the polyamine biosynthetic pathway. It was determined that the metabolic flux indicated by the rate of appearance of fluorinated polyamines, reflected the proliferation status of the cells. U.S. Pat. No. 5,498,522 outlines the use of SSAT enzyme protein, or mRNA transcripts can be measured directly, or other determinants related to SSAT induction can be measured, such as SSAT co-factor acetylCoA, and the SSAT products N1-acetylspermine and N1-acetylspermidine. To further determine the effect of a polyamine analog's administration, an individual can be monitored for disease (or precursor disease) progression as well as biochemical and/or genetic markers of disease (or precursor disease). With respect to disease progression, multiple rating scales (i.e., indices of clinical function) have been established and are known in the art for ALS.

(ii) Antiproliferative Agents

Polyamines play a role in cell growth and proliferation and the induction of cell growth and proliferation has been shown to be associated with a increase in ODC activity and the corresponding increase in the level of putrescine as well as the other polyamines. ODC inhibitors have been used in the treatment of cancer in which they presumably assert their therapeutic effect by blocking polyamine formation, and thereby slowing, interrupting, inhibiting, or stopping the cancer cell proliferation and metastases (See U.S. Pat. Nos. 6,277,411 and 4,499,072).

In recent years growth factors have received a great deal of attention from the ALS research community as a possible means of preventing neuronal death. While neuronal dysfunction or death is certainly the end result of the ALS disease process, great uncertainty remains about the causes of neuronal death. It has been largely assumed that neurons independently become sick or apoptotic. Recent transgenic mouse studies have shown that neuron specific expression of mSOD1 may be insufficient to cause or accelerate disease. Furthermore, chimeric studies mixing mutant and wild-type SOD mice demonstrate that wild-type neurons surrounded by mSOD astrocytes and microglia still die. It is therefore likely that neurons must interact with another cell type in order for disease to occur. While the numbers of viable neurons drops over the disease course, other cells such as astrocytes and microglia become more numerous. Therefore proliferation or activation of these cell types may be responsible for neuronal damage. Reactive astrocytosis, microgliosis and activation of microglia are common hallmarks of many neurodegenerative diseases including ALS. The present invention provides methods and screening assays for pharmacological agents that are capable of reducing reactive astrocytosis, microgliosis, activation of microglia, macrophage proliferation. Pharmacological agents identified through these assays may be useful in treating and/or reducing neurological disorders. Also within the scope is the use of anti-proliferative agents that can also effect the polyamine pathway, such as hydroxyurea and DFMO to ameliorate ALS. In a preferred embodiment, the anti-proliferative agent is hydroxyurea.

Hydroxyurea, an agent approved for the treatment of leukemia and ovarian cancer and currently being studied as a treatment for HIV disease, interferes with viral replication by inhibiting the cellular enzyme ribonucleotide reductase. This inhibition results in a reduction of the supply of the deoxyribonucleotides needed to synthesize new DNA resulting in a decrease in cell proliferation. Ribonucleotide reductase converts ribonucleotides to deoxyribonucleotides, which is essential in DNA synthesis. Inhibition of ribonucleotide reductase can result from the specific interaction of an inhibitor with either of the two subunits of the enzyme. Hydroxyurea, in addition to thiosemicarbazones, 2,3-dihydro-1H-pyrazole[2,3-a]imidazole (IMPY), and several other antitumor agents, inhibits ribonucleotide reductase through its interaction with the smaller subunit (Cory, J. et al. *Adv. Enzyme Regul.* 23, 181–192 (1985)) Hydroxyurea functions at multiple levels to affect a number of different pathways, for example, hydroxyurea is likely to effect ODC activity in the polyamine pathway, to inhibit this enzyme. Hydroxyurea is also an anti-proliferative agent that reduces the proliferation of microglia, astrocytes and neurons. The beneficial effects of DFMO and hydroxyurea are shown in Examples 2, 3 and 6.

In addition to hydroxyurea, other anti-proliferative agents that may affect the polyamine pathway include, but are not limited to, daunomycin, mitomycin C. daunrorubicin, doxorubincin, 5-FU, cytocine arabinoside, colchicine, cytochalasin B, bleomycin, vincristin, vinblastine, methotrexate, cis platinum, ricin, abrin, diptheria toxin, and saporin. These anti-proliferative agents may also function to modulate macrophages.

Other suitable agents are those which affect the closely regulated intracellular concentration of spermidine. An example of such an agent is MGBG (mitoguazone dihydrochloride; XYRKAMINE®; Ilex, Tex.) which inhibits S-adenosylmethionine decarboxylase which in turn is required for the production of polyamines. Any agent that interferes with polyamine interactions with proliferating macrophage target, such as DNA, RNA, and/or membranes would likewise be suitable. Another type of useful agent is one that interferes with polyamine interactions with DNA. Such an agent(s) could exert this function, for example, by any of the effects above (i.e., interfering with the polyamine synthetic pathway and/or metabolism, disturbing the concentration of intracellular spermine, competitors, etc.) as well as affecting polyamine function in terms of interacting with DNA. It is understood that, with respect to these and any other agent described herein, toxicology considerations also must be taken into account when determining whether, and/or in what amount, an agent is to be used.

In one embodiment, pharmacological agents that inhibit cell proliferation may be used to modulate, treat, slow, and/or arrest neurodegencration. In a preferred embodiment, astrocytosis and/or microgliosis is inhibited. Administration of more than one pharmacological agent may be beneficial in the treatment of neurological disorders. Administering both a polyamine pathway inhibitor and an antiproliferative agent is within the scope of the present invention. For example, an ODC inhibitor may produce an additive or synergistic effect with an anti-proliferative agent. Thus, when combination neurological therapy is used, the dosage of the ODC inhibitor may be less than when used alone. In combination with an ODC inhibitor, the anti-proliferative agent may be administered at a lower dosage or at less frequent intervals compared with use of the anti-proliferative agent alone.

(iii) Enzyme Inhibitors

The enzymes of the polymamine pathway may be reversibly inhibited through the noncovalent binding of an inhibitor of at least one of the enzymes of the pathway. This inhibition may be competitive if the inhibitor binds reversibly to the active site of the enzyme, thereby preventing the native substrate from binding. Additionally, if the inhibitor and substrate bind simultaneously to the enzyme without competing for the same binding site, the inhibition may be noncompetitive. If the polyamine pathway is inhibited reversibly, the inhibitor may inhibit different enzymes in the pathway leading to a decrease in at least one of the polyamines selected from the group consisting of putrescine, spermidine, and spermine. An example of a reversible ODC inhibitor is α-methylornithine (T. Thomas et al. *Cell. Mol. Life Sci.* 58: 244–258 (2001)).

Enzyme inhibition may also be irreversible. These inhibitors are highly specific and selective in binding the active site of their target enzyme. Suicide inhibitors form a class of irreversible inhibitors that are activated specifically by their target enzyme. DFMO is a suicide inhibitor of ODC. Non-limiting examples of irreversible ODC inhibitors include, but are not limited to, DFMO, α-halomethyl ornithine, methyl and ethyl esters of monofluoromethyl dehydroornithine, the R, R-isomer of methyl acetylenic putrescine (i.e., (2R, 5R)-6-heptyne-2,5-diamine), amidinoindan-1-one 2'-amidinohydrazone (CGP 48664), optical isomers and combinations thereof. In addition, pharmacological agent is also intended to include other ODC inhibitors with similar structure and function to DFMO that are described by the core formulas:

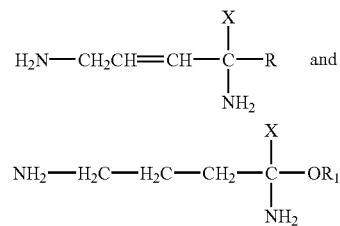

where X is —CHF$_2$ or —CH$_2$F, R is H or COR$_1$, R$_1$ is OH or lower alkoxy groups, and the pharmaceutical acceptable salts and isomers thereof. Other inhibitors of ODC known in the art are described in U.S. Pat. Nos. 4,499,072 and 5,002,879; and the work of Bey et al. ("Inhibition of Basic Amino Acid Decarboxylases Involved in Polyamine Biosynthesis," Inhibition of Metabolism Biological Significance and Basis for New Therapies, McCann et al, eds.; Academic Press, (1987) 1–32). Inhibitors of S-adenosyl-L-methionine decarboxylase are described by Pegg ("Polyamine Metabolism and Its Importance in Neoplastic Growth and as a Target for Chemotherapy," *Cancer Res.* 48: 759–774 (1998)) and Williams-Ashman et al. ("Methylglyoxal Bis(guanylhydrazone) as a Potent Inhibitor of Mammalian and Yesast S-Adenosylmethionine Decarboxylases," *Biochem Biophys. Red. Commun.* 46: 288–295 (1972)).

III. Treatment of Neurodegenerative Disorders Using Polyamine Modulating Drugs

In one aspect, the methods of the invention can be used to modulate, or ameliorate a neurodegenerative disorder. The neurodegenerative disorder is selected from the group consisting of ALS, Creutzfelt Jacob's (CJD), Huntington's (HD), Stroke and Alzheimer's disease (AD). In a preferred embodiment, the neurodegenerative disorder is ALS. In another aspect, the methods of the invention can be used to screen for disregulation or abnormal levels of a polyamine such as putraciene, spermidine and spermine. In a preferred embodiment, the polyamine is putraciene.

Besides astrocytosis, microgliosis, and inflammation, these same diseases also demonstrate significant regional alterations in polyamines and polyamine metabolism. For instance, the enzyme ODC is over-expressed in the injured regions of the AD brain. ODC over-expression has been observed under basal conditions in the Wobbler mouse, one of the animal models of ALS. Human ALS patients show elevated levels of ornithine (the polyamine precursor) in the spinal tissue and arginase (the enzyme which converts arginine to ornithine) in the CSF. Polyamines are integrally involved in cellular proliferation, differentiation signaling, immune cell activation, and cell death. The present invention provides methods and screening assays associating polyamine deregulation to ALS. Polyamine levels were measured in the brain and spinal cords of SOD1 G93A mice demonstrating that polyamines are indeed over expressed.

Examples 2 and 3 demonstrate that polyamine synthesis in the G93A mSOD1 mouse model of ALS can be inhibited with an ODC inhibitor, DFMO, resulting in delayed onset of disease and extension of the life span of the SOD1 G93A mice.

In one aspect of the invention, the polyamine analogs can be incorporated into pharmaceutical compositions suitable for administration to a subject. Typically, the pharmaceutical composition comprises a polyamine analog and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

The pharmaceutical compositions of this invention can be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. The preferred mode of administration is parenteral (e.g., intravenous, subcutaneous, intraperitoneal, intramuscular). In a preferred embodiment, the pharmacological agent is administered by an intraperitoneal injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The polyamine analog can be administered by a variety of methods known in the art. As will be appreciated by the skilled artisan, the route and/or mode of administration will vary depending upon the desired results. In certain embodiments, the polyamine analog can be prepared with a carrier that will protect the analog against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., *Sustained and Controlled Release Drug Delivery Systems*, J. R. Robinson, ed., Marcel Dekker, Inc., New York, 1978; U.S. Pat. Nos. 6,333,051 to Kabanov et al., and 6,387,406 to Kabanov et al.).

In certain embodiments, a polyamine analog of the invention can be orally administered, for example, with an inert diluent or an assimilable edible carrier. The analog (and other ingredients, if desired) can also be enclosed in a hard or soft shell gelatin capsule, compressed into tablets, or incorporated directly into the subject's diet. For oral therapeutic administration, the analogs may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In certain embodiments, a pharmacological agent can be administered in a liquid form. The pharmacological agent is freely soluble in a variety of solvents, such as for example, methanol, ethanol, and isopropanol. The pharmacological agent is, however, highly lipophilic and, therefore, substantially insoluble in water. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of lipophilic compounds such as the pharmacological agent of the present invention.

Supplementary active compounds can also be incorporated into the compositions. In certain embodiments, a pharmacological agent of the invention is coformulated with and/or coadministered with one or more additional therapeutic agents that are useful for improving the pharmacokinetics of the polyamine analog. Methods of improving the pharmacokinetics of the pharmacological agent have been disclosed, for example, in U.S. Pat. Nos. 6,342,250 to Masters, 6,333,051 to Kabanov et al., 6,395,300 to Straub et al., 6,387,406 to Kabanov et al., and 6,299,900 to Reed et al. Masters discloses a drug delivery device and method for the controlled release of pharmacologically active agents and the same methodology maybe used for the polyamine analogs of the present invention. The drug delivery device disclosed by Masters is a film comprising one or more biodegradable polymeric materials, one or more biocompatible solvents, and one or more pharmacologically active agents dispersed uniformed throughout the film. In U.S. Pat. No. 6,333,051, Kabanov et al. disclose a copolymer networking having at least one cross-linked polyamine polymer fragment, at least one nonionic water-soluble polymer fragment, and at least one suitable biological agent, including the pharmacological agent of the present invention. According to the teachings of this patent, this network, referred to as a nanogel network, improves the therapeutic effect of the pharmacological agent by decreasing side effects and increasing therapeutic action. In another patent, U.S. Pat. No. 6,387,406, Kabanov et al. also disclose another composition for improving the oral delivery of numerous pharmacological agents. This delivery vehicle comprises a biological agent and a poly(oxyehtylene)-poly(oxypropylene) block copolymer. Straub et al. disclose porous drug matrices for use with drugs, and in particular, for use with low-aqueous solubility drugs, for enhancing solubility of the drug in an aqueous solution. Reed et al. disclose a drug delivery system, which uses a dermal penetration enhancer to transport a variety of physiologically active agents, including the pharmacological agent of the present invention, across a dermal surface or mucosal membrane of a subject.

Other methods for improving the delivery and administration of the pharmacological agent e.g., a polyamine analog include means for improving the ability of the pharmacological agent to cross membranes, and in particular, to cross the blood-brain barrier. In one embodiment, the pharmacological agent can be modified, e.g., made hydrophobic, to improve its ability to cross the blood-brain barrier, and in an alternative embodiment, the pharmacological agent can be co-administered with an additional agent, such as for example, an anti-fungal compound, that improves the ability of the pharmacological agent to cross the blood-brain barrier. Alternatively, precise delivery of the pharmacological agent into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for pharmacological agent microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The pharmacological agent can be delivered to regions, such as the cells of the spinal cord, brainstem, or brain that are associated with the disease or disorder. For example, target regions can include the medulla, pons, and midbrain, cerebellum, diencephalon (e.g., thalamus, hypothalamus), telencephalon (e.g., corpus stratium, cerebral cortex, or within the cortex, the occipital, temporal, parietal or frontal lobes), or combinations, thereof.

In one aspect of the invention, the pharmacological agent does not cross the blood brain barrier. The proliferating macrophages migrate to the brain leading to the production of microglia and/or astrocytes. Thus, inhibition or suppression of proliferative of macrophages peripherally may prevent or slow neurological disease progression thereby eliminating the need for the pharmacological agent to act in the brain.

In yet another aspect of the invention, the blood brain barrier may be compromised by the elevated production of polyamines associated with neurological disorder such that an effective amount of the pharmacological agent may be able to reach its target site. Polyamines have been shown to play a role in the disruption of the blood-brain barrier (BBB) in various pathological states suggesting that polyamines may play a role as mediators of vasogenic edema formation in the brain following brain injuries (Glantz L et al. *J Basic Clin Physiol Pharmacol* 7:1–10 (1996)).

Pharmacological agents can be used alone or in combination to treat neurodegenerative disorders. For example, the pharmacological agent can be used in conjunction with polyamine analogs or other ODC inhibitors, for example, to produce a synergistic effect. Likewise, the pharmacological agent can be used alone or in combination with an additional agent, e.g., an agent which imparts a beneficial attribute to the therapeutic composition, e.g., an agent which effects the viscosity of the composition. The combination can also include more than one additional agent, e.g., two or three additional agents if the combination is such that the formed composition can perform its intended function.

The pharmaceutical compositions of the invention can include a "therapeutically effective amount" or a "prophylactically effective amount" of a pharmacological agent of the invention. A "therapeutically effective amount" refers to an amount effective, at dosages and for periods of time necessary, to achieve the desired therapeutic result. A therapeutically effective amount of the pharmacological agent can vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a pharmacological agent of the invention is between 100 mg/Kg/day and 10,000 mg/Kg/day, administered to a subject. Preferably, administration of a therapeutically effective amount of pharmacological agent results in a concentration of pharmacological agent in the bloodstream that is between about 0.1 μM and 1000 μM. Preferably, the concentration of pharmacological agent in the blood is between about 1–100 μM. More preferably, the concentration of pharmacological agent in the blood is between about 1–50 μM. It is to be noted that dosage values can vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV. Screening Assay for Pharmacological Agents

The methods of the invention can be used to screen a large number of candidate compositions to find pharmacological agents capable of modulating polyamine levels in a subject. The screening assay methods of the present invention are preferably cellular assays that include a cell line that can be stably cultured using standard cell culture techniques known to those having ordinary skill in the art. For example, the screening assay methods of the present invention can include the steps of (i) determining the polyamine level in a substrate, (ii) applying a pharmacological agent to the substrate, and (iii) measuring changes in the polyamine level in response to the applied pharmacological agent.

In one embodiment, the assay will identify pharmacological agents that decrease polyamine levels in proliferating immune cells of all types. In another embodiment, assays and methods are disclosed for screening for pharmacological agents that are capable of reducing the levels of polyamine levels in the brain and spinal cord of neurological afflicted subjects. The method comprises obtaining non-transgenic wild-type mice as well as symptomatic and asymptomatic G93A SOD1 mice, administering a pharmacological agent and a control to a group of each mouse population, sacrificing the mice, homogenizing the brain and spinal cord, quantitating the level of polyamine levels present in each tissue, and comparing the polyamine levels between the mouse populations. Pharmacological agents that are found to decrease polyamine levels when compared to the control population are possible drug candidates.

The term "measuring the difference in the polyamine level" or "measuring the difference in polyamine expression," as used herein, refers to any means or methods of comparison between the level of polyamine activity in a substrate prior to the application of a pharmacological agent and the level of polyamine application after application of the pharmacological agent. A statistically significant difference in the polyamine level can be a difference in values by a factor of 10 between the test sample and the control sample, more preferably, a difference by a factor of 8, even more preferably, a difference by a factor of 6, even more preferably, a difference by a factor of 4, and most preferably, a difference by a factor of 2.

The screening assay method of the present invention can be run under normal conditions, or alternatively, the screening assay can be run in the presence various stress models. Preferable stress models include, but are not limited to, heat shock models and oxidative stress models. According to the present invention, the stress models can be introduced either before or after the application of a pharmacological agent to the substrate.

Equivalents

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

EXAMPLES

The following examples illustrate that the pharmacological agent of the present invention, e.g., DFMO and DENSPM, delay the disease progression and prolongs the life of male SOD1 G93A mice. The beneficial effect of DFMO in the SOD1 G93A mouse model demonstrates that the polyamine biosynthetic pathway is a novel target for drug discovery in ALS. The following examples are merely illustrative of the present invention and should not be construed so as to limit the scope of this invention.

Example 1

Methods and Materials
(i) Model Description: The SOD1 G93A (high copy) mouse model was used as the model for ALS. This mouse model carries 25 copies of the human G93A SOD mutation and is driven by the endogenous promoter. Survival in the mouse is copy dependent. The high copy G93A has a median survival of around 128 days. High molecular weight complexes of mutant SOD protein are seen in the spinal cord beginning around day 30. At day 60 reactive astrocytosis (GFAP reactive) are observed; activated microglia are observed from day 90 onwards. Studies by Gurney et al. showed that at day 90 reactive astrocytosis loses statistical significance while microglial activation is significantly elevated and continues to be elevated through the end stage of the disease.

Many drugs that have shown efficacy in this model have move forward into human clinical trials based on the data resulting form studies with this model. Experience with riluzole, the only approved drug in the treatment of ALS, indicates that the mouse ALS model is a good predictor of clinical efficacy.

(ii) Murine FALS model: Heterozygous transgenic mice carrying the human SOD-1 (G93A) gene were obtained from Jackson Laboratory (Bar Harbor, Me., USA).

(iii) Pharmacological agent: Difloromethylornithine (DFMO) is an irreversible inhibitor of the enzyme ornithine decarboxylase (ODC), the rate-limiting enzyme in polyamine biosynthesis. DFMO is approved as Ornidyl for the treatment of African Sleeping Sickness. DFMO was obtained in oral form from ILEX Oncology, Inc (San Antonio, Tex.).

(iv) Methods: Forty (n=40) SOD1 G93A high copy mice obtained from Jackson Laboratory (Bar Harbor, Me.) were separated into two groups of twenty (n=20) with an equal number of males (n=10) and females (n=10) in each group. The groups were also litter matched to reduce group variation. Male animals were singly housed and females were group housed to conserve space. Animals received standard rodent chow and water while they were able to feed themselves. When animals had difficulty in moving and taking care of themselves chow and water were replaced with food pellets in bedding and Jell-O for water.

(v) Pharmacological Agent Delivery: All pharmacological agents were administered to SOD1 G93A mice. DFMO was delivered according to a chronic delivery protocol applied in the human glioblastoma trial (UCSF Clinical trial protocol of ALS).

In Example 2, the animals were dosed at 3200 mg/Kg/day of DFMO in drinking water for 21 days followed by a 7 day drug holiday (no DFMO). In Example 3, the animals were continually dosed at 3200 mg/Kg/day of DFMO in drinking water. Controls animals were given water as vehicle. All treatments are performed 7 days per week and treatment was initiated at day 60 of life. The treated group continued to receive 3200 mg/kg/day of DFMO in drinking water until a neurological score of 2 (See section (vi) below) at which point drug was delivered via intraperitineal injection (IP) injection. When a neurological score of 2 is attained, the animals are no longer capable of drinking themselves due to paralysis. At this point, the same dosage of DFMO is administered to the animal in IP injection form. Controls were given water as vehicle until a neurological score of 2 at which point they were injected with saline as vehicle.

In Example 6, hydroxyurea was administered by intraperitineal injection at a dose of 250 mg/Kg/day once daily for 7 days a week, beginning at day 50 until day 110. The treatment was discontinued after day 110 due to toxicity arising from the hydroxyurea. Despite, the toxicity related to the drug, the hydroxyurea still continued to provide a protective effect in terms of prolonging the lifespan of the animal. Cytotoxicity resulting from the drug can readily be identified from the protective effects of the drug by observing signs of toxicity such as neutrophenia, thrombocytopenia and haemolysis. The cytotoxic effects of hydroxyurea can be reduced by altering and optimizing the dose of the drug that is administered to the animal.

In Example 7, DENSPM was administered by intraperitineal injection at a dose of 24 mg/kg/day twice daily for 7 days a week till death.

(vi) Neurological Scoring: Neurological score of each limb was monitored and recorded according to a defined 4-point scale defined below:

0=Normal reflex on the hind limbs (animal will splay its hind limbs when lifted by its tail).

1=Abnormal reflex of hind limbs (lack of splaying of hind limbs when animal is lifted by the tail).

2=Abnormal reflex of limbs and evidence of paralysis.

3=Lack of reflex and complete paralysis.

4=Inability to right themselves when placed on the sides in 30 seconds or found dead. The animals are sacrificed at this stage if alive.

(vii) End Points and Statistics: The primary end point is survival with secondary end points of neurological score and body weight. Neurological score observations and body weight are made and recorded five days per week.

(viii) Statistical Analysis: Statistical analysis on body weight and neurological score was performed using mixed linear model repeated measure ANOVA. Survival analysis was performed by Kaplan-Meier analysis using the frailty model for sex and litter correction.

Example 2

Figure 2:
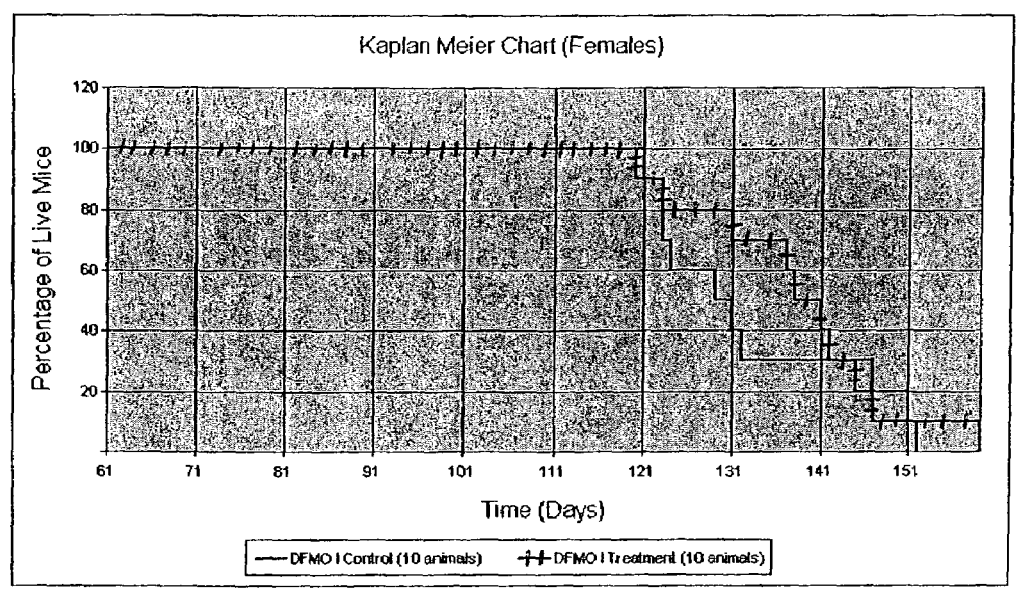
FIG. 2 is a graph showing the effect of discontinuous DFMO delivery on survival of female SOD1 G93A mice.
Figure 3:
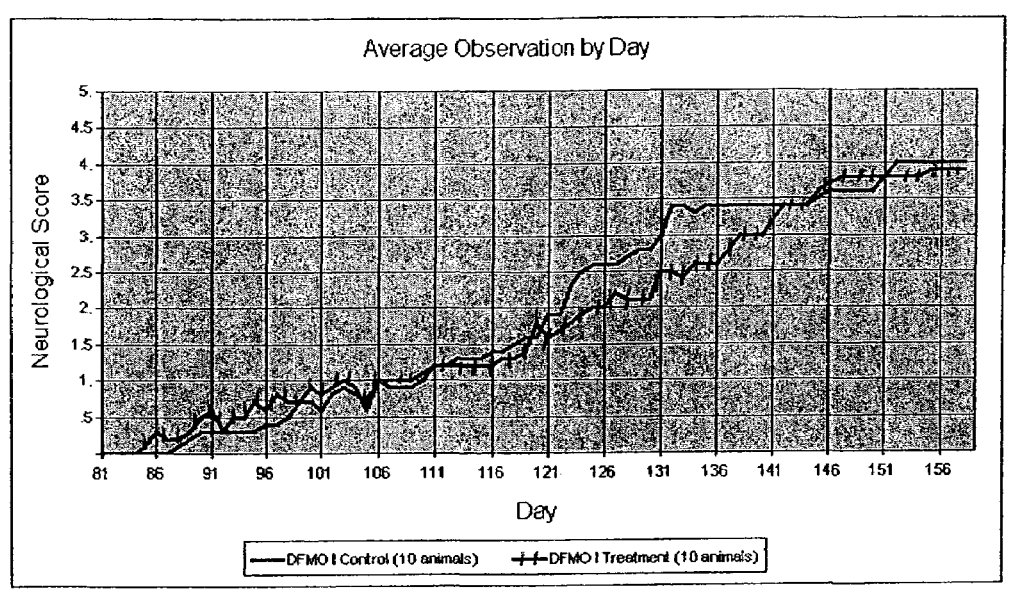
FIG. 3 is a graph showing the effect of discontinuous DFMO delivery on the neurological progression of female SOD1 G93A mice.

Treatment of ALS in a SOD-1 (G93A) Mouse Model with Discontinuous Dosing of DFMO During this study, DFMO was delivered chronically at a dose of 3200 mg/Kg/day in drinking water for 21 days followed by a 7 day drug holiday (no drug) according to the methods described in Example 1. Results are shown in FIGS. 2 and 3 and described below.

Percent Survival Analysis: In the females 70% of the deaths of animals in the treatment group occurred during the time of drug holiday or a few days immediately succeeding the holiday. However, only 30% of deaths occurred in the control group during the same period (FIG. 2). DFMO, a substrate analog inhibitor of ornithine decarboxylase delays the onset of disease and extends the survival of the SOD1 G93A mouse.

Neurological Score analysis: No effect was seen in the combined results or in the male mice (data not shown). However, discontinuous delivery of DFMO was protective in the female SOD1 G93A mouse during the course of drug delivery period. The total female effect was 3.5% as shown in FIG. 3. The female mice showed a positive trend sufficient to warrant screening DFMO again with no drug holiday (shown in Example 3). The lack of effect observed in this study in the male mice may be a reflection of the varying amount of polyamines between different genders. For example, a higher base level of polyamines in males may require a higher or longer dosage of DFMO before the positive effect of the pharmacological agent can be observed. This hypothesis is being explored in ongoing studies.

Example 3

Treatment of ALS in a SOD-1 (G93A) Mouse Model with Continuous Dosing of DFMO

During this study, DFMO was delivered chronically at a dose of 3200 mg/Kg/day in drinking water for 21 days without any drug holiday until death according to the methods described in Example 1. Results are shown in FIGS. 4–9 and described below.

Percent Survival Analysis: DFMO extended the life span of the SOD1 G93A mice as shown in FIGS. 4, 6 and 8. DFMO, a substrate analog inhibitor of ornithine decarboxylase delays the onset of disease and extends the survival of the SOD1 G93A mouse.

Neurological Score analysis: Continuous delivery of DFMO was protective in the combined results of the male and female SOD1 G93A (FIG. 5) as well as in the male (FIG. 7) and female (FIG. 9) SOD1 G93A population. The total combined effect was 9.69% ($p=0.02$) when analyzed by Cox proportional hazard using litter effect as a frailty term. The male mice showed an 8.21% effect while the female mice showed an 11.48% effect. Thus, when DFMO was delivered continuously, a positive trend was observed regardless of gender.

Collectively, these results demonstrate that the polyamine putrescine is high in female mice and that inhibiting putrescine synthesis with DFMO has a beneficial and reproducible effect. Studies are currently underway to analyze polyamines in male vs. female mSOD1 mice and wild-type mice. While positive effects are seen in male mice, the effect is less reliable at current doses. Differences in polyamine synthesis and regulation exist between the sexes and may account for the different observed effects. The positive male trend in the ongoing IP injection study using 3200 mg/kg of DFMO, suggests that this may be true. Higher plasma concentration of DFMO can be achieved by systemic delivery as opposed to oral delivery.

In conclusion, ODC inhibitor Eflornithine (DFMO) treated animals show signs of improved survival. These data demonstrate a target in ALS that can be exploited for drug development.

Example 4

In Vitro Analysis of Modulation of Cell Proliferation in Neurodegenerative Disorders This example demonstrates how cells can be monitored and screened for a decrease in proliferation following the addition of a pharmacological agent. One non-limiting example of a proliferation assay that may be performed is described. Cells can be seeded in culture dishes, induced to proliferation, treated with either a pharmacological agent or PBS, and allowed to progress in the cell cycle. Following a determined amount of time, [$^3$H]thymidine is added to the medium. After 1 hour at 37° C., the cells are washed with PBS and the radioactive thymidine incorporation in cellular DNA was quantified by liquid scintillation counting. Alternatively cell proliferation can be measured by detecting proliferation marker(s) and/or the uptake of substances such as [$^3$H]thymidine, BrdU, and tetrazolium salts (e.g., MTT and XTT).

Example 5

In Vitro Analysis of Modulation of Polyamine Levels in Neurodegenerative Disorders This example demonstrates how cells can be monitored for a decreased levels of polyamines following the addition of a pharmacological agent. The following are non-limiting examples of assays for measuring polyamine levels that may be performed.

Cells can be treated as described above for the proliferation assay (See Example 4). The cells can then be harvested and the cell pellets are acidified and sonicated. The solution can be incubated on ice and centrifuged to remove the precipitated proteins. Intracellular polyamine levels can be determined by known HPLC techniques as described previously by (Thomas et al. *Breast Cancer Research and Treatment* 39: 293–306 (1996)).

Alternatively, brain and spinal cord tissue can be collected from symptomatic SOD1 G93A, pre-symptomatic SOD1 G93A, and non-transgenic (wild-type) mice. The tissue can be homogenized in acid containing an internal standard (i.e. diamioheptane or 1,6-diaminohexane), centrifuged, and stored frozen prior to analysis. Polyamines can then be quantitated by known HPLC techniques of the DANSYL derivatives with fluorescence detection as described above.

Example 6

Treatment of ALS in a SOD-1 (G93A) Mouse Model with Hydroxyurea

Figure 10:
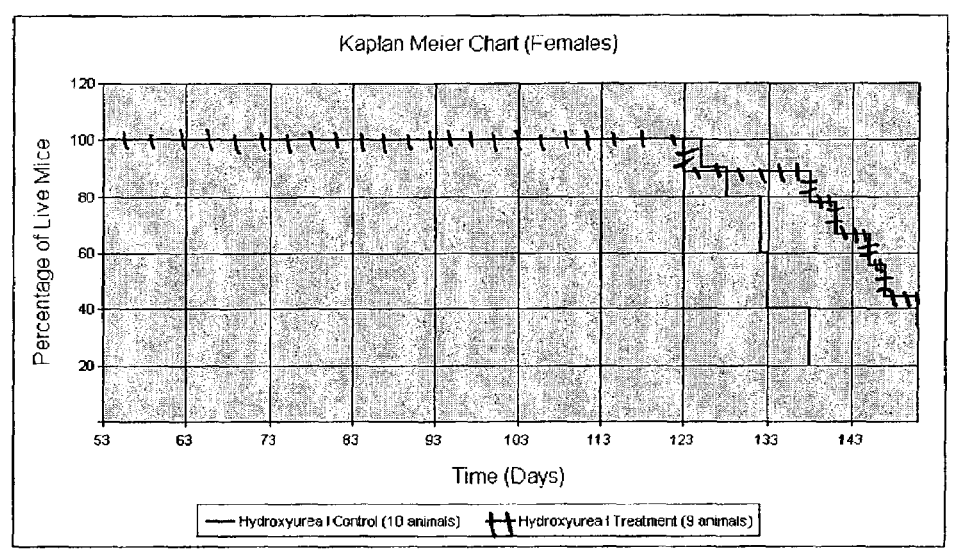
FIG. 10 is a graph showing the effect of hydroxyurea, an anti-proliferative agent with ribonucleotide reductase inhibitor activity, on survival of female SOD1 G93A mice.
Figure 11:
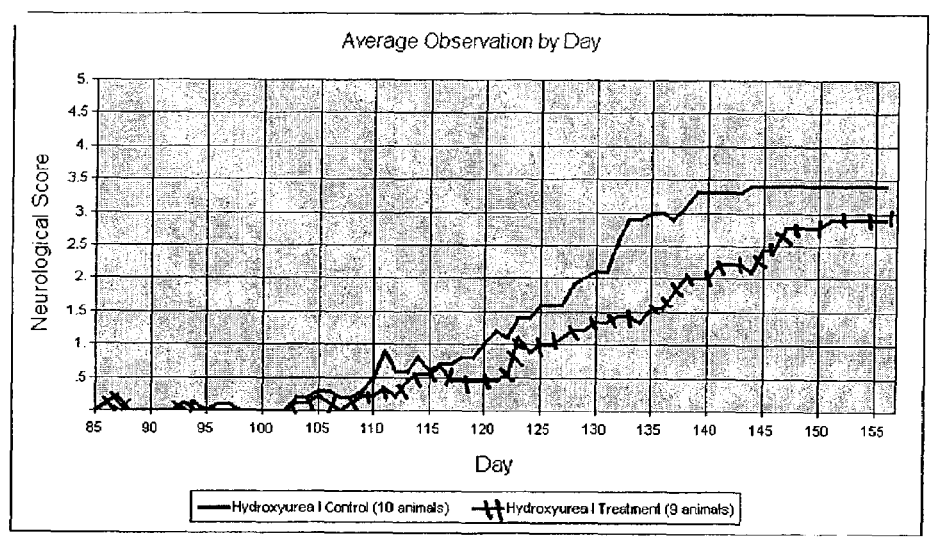
FIG. 11 is a graph showing the effect of hydroxyurea, an anti-proliferative agent with ribonucleotide reductase inhibitor activity, on ALS disease progression of female SOD1 G93A mice.

This example demonstrates the in vivo protective effect of hydroxyurea in ALS using SOD-1 (G93A) mice. During this study, hydroxyurea was given by intraperitineal injection at 250 mg/Kg/day once daily for 7 day a week from day 50 until day 110 days as described in Example 1. The treatment was discontinued after day 110 due to toxicity arising from the hydroxyurea. Despite, the toxicity related to the hydroyurea, the hydroxyurea still continued to provide a protective effect in terms of prolonging the lifespan of the animal. Cytotoxicity resulting form the drug can readily be identified from the protective effects of the drug by observing signs of toxicity such as neutrophenia, thrombocytopenia and haemolysis. The cytotoxic effects of hydroxyurea can be reduced by altering and optimizing the dose of the drug that is administered to the animal. The results are shown in FIGS. 10 and 11 and described below.

Percent Survival Analysis: Hydroxyurea extended the life span of the SODI G93A mice as shown in FIG. 10. The effects were statistically and quantitatively similar to those observed with animals treated with DFMO (See Example 2 and 3). Hydroxyurea delays the onset of ALS disease and extends the survival of the SOD1 G93A mouse. Hydroxyurea is an anti-proliferative agent, a ribonucleotide reductase inhibitor, and may also be involved in the polyamine pathway, possibly acting to inhibit ODC.

Neurological Score analysis: Delivery and treatment with hydroxyurea was protective in the female (FIG. 11) SOD1 G93A population. These results demonstrate that the hydroxyurea may be inhibiting neurons form proliferating, in particular by reducing proliferation of astrocytes and microglia. Similar results are anticipated in male SOD1 G93A mice.

Example 7

Treatment of ALS in a SOD-1 (G93A) Mouse Model with DENSPM

Figure 12:
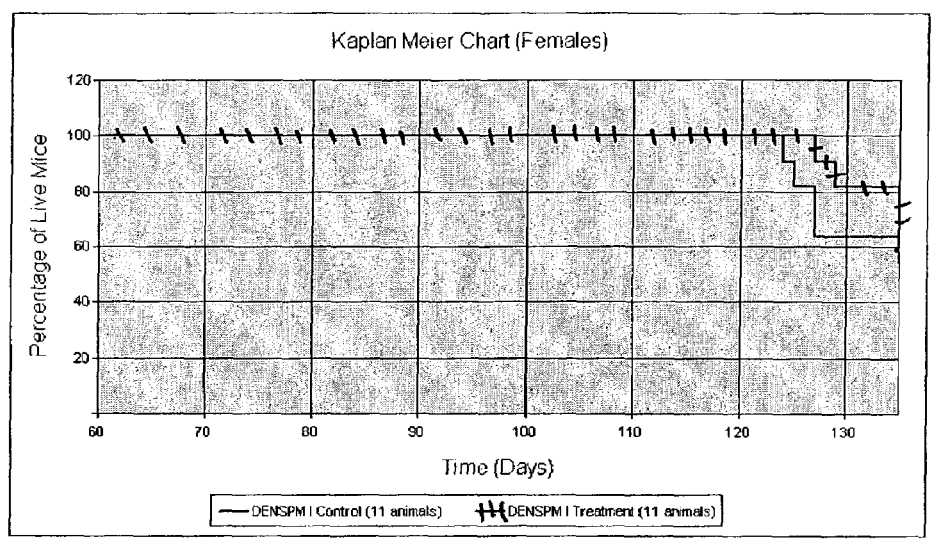
FIG. 12 is a graph showing the effect of DENSPM, a polyamine analog with anti-proliferative activity, on survival of female SOD1 G93A mice.
Figure 13:
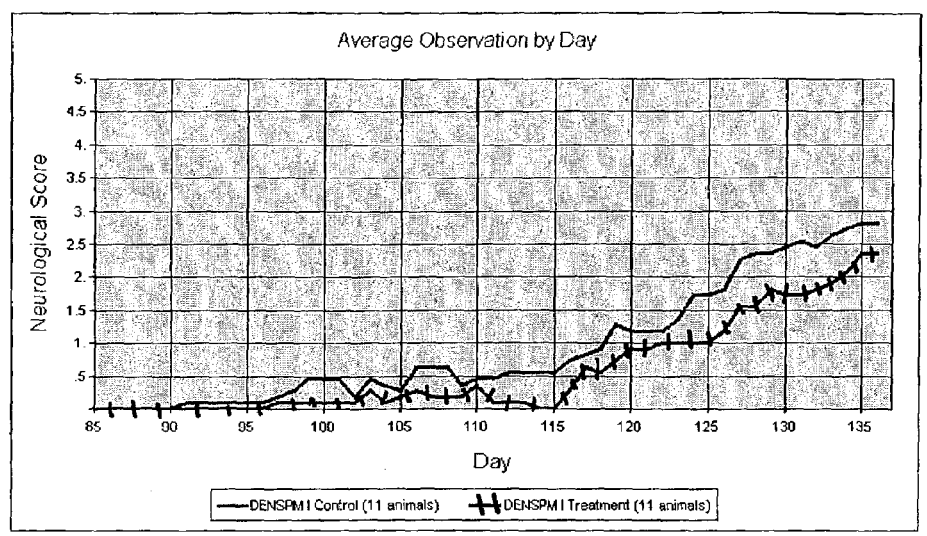
FIG. 13 is a graph showing the effect of DENSPM, a polyamine analog with anti-proliferative activity, on ALS disease progression of female SOD1 G93A mice.

This example demonstrates the in vivo protective effect of DENSPM in ALS using SOD-1 (G93A) mice. During this study, DENSPM was delivered through intraperitoneal injection at 24 mg/kg/day twice daily for 7 days a week, till death according to the methods described in Example 1. Results are shown in FIGS. 12 and 13 and described below.

Percent Survival Analysis: DENSPM, a polyamine analog with anti-proliferative activity, delays the onset of disease and extends the survival of female SOD1 G93A mouse, as shown in FIG. 12. DENSPM mimics the polyamine, operating in a negative feedback mechanism to trick the cell into "thinking" there is sufficient levels of the polyamine present, thus shutting down the polyamine synthesis pathway. Similar results are expected in male SOD1 G93A mice.

Neurological Score analysis: Delivery of DENSPM was protective in the female SOD1 G93A population (FIG. 13). Similar results are expected in male SOD1 G93A mice.

Collectively, these results demonstrate that the symptoms of ALS can be modulated by administering modulating agents. In particular, the results show that the pharmacological agent, DFMO, inhibits the ODC enzyme and affects the levels of putrescine; the polyamine analog, DENSPM, which regulates a negative feedback mechanism tricking the cell to stop synthesizing polyamines; and hydroxyurea, which acts via an unknown mechanism to inhibit ODC, ribonucleotide reductase, and cell proliferation. All of the modulating agents appear to affect the polyamine biosynthesis pathway and provide protection against ALS.

What is claimed is:

1. A method for ameliorating progression of amyotrophic lateral sclerosis (ALS) in a subject comprising administering to the subject a therapeutically effective amount of a modulating agent that modulates at least one enzyme in the polyamine pathway, such that the modulation produces an amelioration in the progression of ALS, wherein the modulating agent is hydroxyurea.

2. The method of claim 1, wherein the modulating agent is administered as a pharmaceutical composition.

3. The method of claim 1, wherein the modulating agent is administered via an oral route.

4. The method of claim 1, wherein the modulating agent is administered via an intravenous route.

* * * * *